(12) United States Patent
Daugharthy et al.

(10) Patent No.: US 12,297,499 B2
(45) Date of Patent: May 13, 2025

(54) MULTICOMPONENT NUCLEIC ACID PROBES FOR SAMPLE ANALYSIS

(71) Applicant: 10x Genomics, Inc., Pleasanton, CA (US)

(72) Inventors: Evan Daugharthy, Cambridge, MA (US); Richard Terry, Carlisle, MA (US); Soo Hee Lee, Somerville, MA (US); Michele A. Busby, Needham, MA (US); Shoshoni Droz, Boston, MA (US); Ryan Gilmore, Somerville, MA (US)

(73) Assignee: 10X GENOMICS, INC., Pleasanton, CA (US)

( * ) Notice: Subject to any disclaimer, the term of this patent is extended or adjusted under 35 U.S.C. 154(b) by 885 days.

(21) Appl. No.: 17/403,169

(22) Filed: Aug. 16, 2021

(65) Prior Publication Data

US 2022/0049302 A1 Feb. 17, 2022

Related U.S. Application Data

(60) Provisional application No. 63/066,707, filed on Aug. 17, 2020.

(51) Int. Cl.
*C12Q 1/6876* (2018.01)
*C12Q 1/6832* (2018.01)

(52) U.S. Cl.
CPC ......... *C12Q 1/6876* (2013.01); *C12Q 1/6832* (2013.01)

(58) Field of Classification Search
CPC ............................ C12Q 1/6832; C12Q 1/6876
See application file for complete search history.

(56) References Cited

U.S. PATENT DOCUMENTS

| | | | |
|---|---|---|---|
| 5,635,352 A | 6/1997 | Urdea et al. |
| 5,695,940 A | 12/1997 | Drmanac et al. |
| 6,054,274 A | 4/2000 | Sampson et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,323,009 B1 | 11/2001 | Lasken et al. |
| 6,344,329 B1 | 2/2002 | Lizardi et al. |
| 6,368,801 B1 | 4/2002 | Faruqi |
| 6,534,266 B1 | 3/2003 | Singer |
| 7,255,994 B2 | 8/2007 | Lao |

(Continued)

FOREIGN PATENT DOCUMENTS

| WO | WO-2012099896 A2 * | 7/2012 | ........... C12Q 1/6804 |
|---|---|---|---|
| WO | WO 2017/143155 | 8/2017 | |

(Continued)

OTHER PUBLICATIONS

Allawi et al., "Thermodynamics and NMR of internal G.T mismatches in DNA," Biochemistry, (1997) 36:10581-94.

(Continued)

*Primary Examiner* — Samuel C Woolwine
*Assistant Examiner* — Lisa Horth
(74) *Attorney, Agent, or Firm* — MORRISON & FOERSTER LLP

(57) ABSTRACT

The present disclosure provides methods, systems, compositions, and kits for analyzing target molecules, including using probes comprising a plurality of components for analyzing target molecules in situ in a sample.

20 Claims, 8 Drawing Sheets

(56) References Cited

U.S. PATENT DOCUMENTS

| | | |
|---|---|---|
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,655,898 B2 | 2/2010 | Miller |
| 7,893,227 B2 | 2/2011 | Wu et al. |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2009/0088327 A1 | 4/2009 | Rigatti et al. |
| 2009/0325172 A1 | 12/2009 | Milton et al. |
| 2010/0028885 A1 | 2/2010 | Balasubramanian et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239874 A1* | 7/2020 | Mikkelsen ........... C12Q 1/6806 |
| 2020/0239946 A1 | 7/2020 | Dewal |
| 2020/0332368 A1 | 10/2020 | Ferree et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |

(56) References Cited

U.S. PATENT DOCUMENTS

| | | |
|---|---|---|
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | | | |
|---|---|---|---|---|
| WO | WO-2019038372 A1 * | 2/2019 | ............ | C12Q 1/6806 |
| WO | WO 2019/199579 | 10/2019 | | |
| WO | WO 2020/076976 | 4/2020 | | |
| WO | WO 2020/076979 | 4/2020 | | |
| WO | WO 2020/096687 | 5/2020 | | |
| WO | WO 2020/099640 | 5/2020 | | |
| WO | WO 2020/117914 | 6/2020 | | |
| WO | WO 2020/123316 | 6/2020 | | |
| WO | WO 2020/123742 | 6/2020 | | |
| WO | WO 2020/142490 | 7/2020 | | |
| WO | WO 2020/240025 | 12/2020 | | |
| WO | WO 2020/254519 | 12/2020 | | |
| WO | WO 2021/123282 | 6/2021 | | |
| WO | WO 2021/123286 | 6/2021 | | |
| WO | WO 2021/138676 | 7/2021 | | |
| WO | WO 2021/155063 | 8/2021 | | |
| WO | WO 2021/168326 | 8/2021 | | |
| WO | WO 2023/108139 | 6/2023 | | |
| WO | WO 2023/141476 | 7/2023 | | |
| WO | WO 2023/172915 | 9/2023 | | |
| WO | WO 2023/192302 | 10/2023 | | |
| WO | WO 2024/148300 | 7/2024 | | |

OTHER PUBLICATIONS

Archer et al., "Selective and flexible depletion of problematic sequences from RNA-seq libraries at the cDNA stage," BMC Genomics. (2014) 15(1):401.

Baner et al., "Signal amplification of padlock probes by rolling circle replication," Nucleic Acids Res. (1998) 26(22):5073-5078.

Bolognesi et al., "Multiplex Staining by Sequential Immunostaining and Antibody Removal on Routine Tissue Sections," J. Histochem. Cytochem. (2017); 65(8): 431-444.

Chen et al., "Nanoscale imaging of RNA with expansion microscopy," Nat Methods. (2016) 13:679-684.

Chen et al., "Expansion Microscopy," Science (2015) 347(6221):543-548.

Dean et al., "Rapid Amplification of Plasmid and Phage DNA Using Phi29 DNA Polymerase and Multiply-Primed Rolling Circle Amplification," Genome Research (2001) 11:1095-1099.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Kanehisa, "Use of statistical criteria for screening potential homologies in nucleic acid sequences," Nucleic Acids Res. (1984) 12:203-213.

Kuhn et al. "Template-independent ligation of single-stranded DNA by T4 DNA ligase." *The FEBS journal* 272.23 (2005): 5991-6000.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

McGinn et al., "New technologies for DNA analysis—a review of the READNA Project," N Biotechnol. (2016) 33(3): 311-30. doi: 10.1016/j.nbt.2015.10.003.

Mohsen et al., "The Discovery of Rolling Circle Amplification and Rolling Circle Transcription," Acc Chem Res. (2016) 49(11): 2540-2550.

(56) References Cited

OTHER PUBLICATIONS

Nallur et al., "Signal amplification by rolling circle amplification on DNA microarrays," Nucleic Acids Res. (2001) 29(23): e118.

Payne et al. "In situ genome sequencing resolves DNA sequence and structure in intact biological samples," Science. (2021) 371(6532): eaay3446. doi: 10.1126/science.aay3446. Epub Dec. 31, 2020.

Pirici et al., "Antibody elution method for multiple immunohistochemistry on primary antibodies raised in the same species and of the same subtype," J Histochem Cytochem. (2009) 57(6); 567-75.

Rouhanifard et al. "ClampFISH detects individual nucleic acid molecules using click chemistry-based amplification," Nat Biotechnol. (2018) 17 pages. doi: 10.1038/nbt.4286.

Schweitzer et al., "Multiplexed protein profiling on microarrays by rolling-circle amplification," Nature Biotech. (2002) 20:359-365.

Schweitzer et al. "Immunoassays with rolling circle DNA amplification: A versatile platform for ultrasensitive antigen detection," Proc. Natl. Acad. Sci. USA (2000) 97:10113-119.

Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.

Vandernoot et al., "cDNA normalization by hydroxyapatite chromatography to enrich transcriptome diversity in RNA-seq applications," Biotechniques, (2012) 53(6) 373-80.

Wu, C. et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.

Bibikova et al., "Quantitative gene expression profiling in formalin-fixed, paraffin-embedded tissues using universal bead arrays," Am J Pathol. Nov. 2004;165(5):1799-807.

Capodieci et al., "Gene expression profiling in single cells within tissue," Nat Methods. (2005) 2(9): 663-5.

Chen et al., "Efficient in situ barcode sequencing using padlock probe-based BaristaSeq," Nucleic Acids Res. (2018) 46(4): e22.

Conze et al., "Single molecule analysis of combinatorial splicing," Nucleic Acids Res. (2010) 38(16): e163.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Lagunavicius et al., "Novel application of Phi29 DNA polymerase: RNA detection and analysis in vitro and in situ by target RNA-primed RCA," RNA. (2009) 15(5):765-71.

Larsson et al. "In situ detection and genotyping of individual mRNA molecules," Nat Methods. (2010) 7(5):395-397.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Maierhorfer et al., "Multicolor deconvolution microscopy of thick biological specimens," Am J Pathol. (2003) 162(2): 373-9.

Meade et al. "Multiplexed DNA detection using spectrally encoded porous SiO2 photonic crystal particles," Anal Chem. (2009) 81(7): 2618-25.

Raj et al., "Imaging individual mRNA molecules using multiple singly labeled probes," Nat Methods. (2008) 5(10): 877-879.

Sun et al., "Composite organic-inorganic nanoparticles as Raman labels for tissue analysis," Nano Lett. (2007) 7(2): 351-6.

Sun et al., "Integrating barcoded neuroanatomy with spatial transcriptional profiling enables identification of gene correlates of projections," Nat Neurosci. (2021) 24(6):873-885.

Wählby et al., "Sequential immunofluorescence staining and image analysis for detection of large numbers of antigens in individual cell nuclei," Cytometry. (2002) 47(1): 32-41.

Weibrecht et al., "Simultaneous visualization of both signaling cascade activity and end-point gene expression in single cells," PLoS One. (2011) 6(5): e20148.

Wilson et al., "Encoded microcarriers for high-throughput multiplexed detection," Angew Chem Int Ed Engl. (2006) 18;45(37): 6104-17.

Zhao et al., "Advances of multiplex and high throughput biomolecular detection technologies based on encoding microparticles," Sci China Chem. (2011) 54(8):1185.

* cited by examiner

600

┌─────────────────────────────────────┐
│ Hybridize a plurality of probe components │
│ to a target molecule, hybridize a splint │ ─── 610
│ component to the plurality of probe │
│ components, and perform a gap fill and/or │
│ ligation reaction on the plurality of probe │
│ components │
└─────────────────────────────────────┘
                    ↓
┌─────────────────────────────────────┐
│ Conduct an amplification reaction   │ ─── 620
└─────────────────────────────────────┘
                    ↓
┌─────────────────────────────────────┐
│ Detect a product of the amplification │ ─── 630
│ reaction │
└─────────────────────────────────────┘

*FIG. 6*

MULTICOMPONENT NUCLEIC ACID PROBES FOR SAMPLE ANALYSIS

CROSS-REFERENCE TO RELATED APPLICATION

This application claims priority to U.S. provisional application 63/066,707, filed Aug. 17, 2020, entitled "SYSTEMS, METHODS, AND COMPOSITIONS FOR SAMPLE ANALYSIS," which application is incorporated by reference in its entirety for all purposes.

BACKGROUND

Biological sample analysis, including nucleic acid analysis, has emerged as an important process for a variety of fields of endeavor, such as personalized medicine, cancer and disease research, and evolutionary biology. Understanding the identity of the sample, such as the presence of a particular nucleic acid sequence or other biological molecule is valuable to researchers and scientists, helping them understand better the basic components of biological systems.

SUMMARY

Methods are available for analyzing nucleic acids in a biological sample in situ, such as a cell or a tissue. For instance, advances in single molecule fluorescent hybridization (smFISH) have enabled nanoscale-resolution imaging of RNA in cells and tissues. However, oligonucleotide probe-based assay methods for in situ analysis may suffer from low sensitivity, specificity, and/or detection efficiency and may require careful and laborious optimization. Improved systems, methods, compositions, and kits for sample analysis such as in situ assays are needed. The present disclosure addresses these and other needs.

In some embodiments, disclosed herein is a method for analyzing a sample, comprising forming a hybridization complex comprising a first nucleic acid molecule (e.g., a first probe), a second nucleic acid molecule (e.g., a second probe), a third nucleic acid molecule (e.g., a splint), and a target nucleic acid molecule in the sample, wherein: the target nucleic acid molecule comprises a first target sequence and a second target sequence; the third nucleic acid molecule (e.g., the splint) comprises a sequence (e.g., a first splint sequence) and an additional sequence (e.g., a second splint sequence): the first nucleic acid molecule (e.g., the first probe) comprises, from one end to another: (i) a first nonhybridizing region (e.g., a first splint-hybridizing region) forming a first duplex with the sequence (e.g., the first splint sequence) and (ii) a first hybridizing region (e.g., a first target-hybridizing region) hybridized to the first target sequence; the second nucleic acid molecule (e.g., the second probe) comprises, from one end to another: (i) a second hybridizing region (e.g., a second target-hybridizing region) hybridized to the second target sequence, (ii) a barcode region corresponding to the target nucleic acid molecule, and (iii) a second nonhybridizing region (e.g., a second splint-hybridizing region) forming a second duplex with the additional sequence (e.g., the second splint sequence); and the first duplex and the second duplex differ in stability.

In some embodiments, the method further comprises coupling (e.g., ligating) the first nonhybridizing region (e.g., the first splint-hybridizing region) and the second nonhybridizing region (e.g., the second splint-hybridizing region). In any of the preceding embodiments, the method may further comprise coupling (e.g., ligating) the first hybridizing region (e.g., the first target-hybridizing region) and the second hybridizing region (e.g., the second target-hybridizing region). In some embodiments, the method may comprise generating a nucleic acid product (e.g., a ligated product such as a circular probe) by (i) coupling (e.g., ligating) the first hybridizing region (e.g., the first target-hybridizing region) and the second hybridizing region (e.g., the second target-hybridizing region) and/or (ii) coupling (e.g., ligating) the first nonhybridizing region (e.g., the first splint-hybridizing region) and the second nonhybridizing region (e.g., the second splint-hybridizing region).

In any of the preceding embodiments, the method may further comprise determining a sequence of the barcode region or complement thereof in the nucleic acid product or an amplification product thereof, thereby detecting the target nucleic acid molecule in the sample.

In some embodiments, disclosed herein is a method for analyzing a sample, comprising forming a hybridization complex comprising a first probe, a second probe, a splint, and a target nucleic acid molecule in the sample, wherein: the target nucleic acid molecule comprises a first target sequence and a second target sequence; the splint comprises a first splint sequence and second splint sequence; the first probe comprises, from one end to another: (i) a first splint-hybridizing region forming a first duplex with the first splint sequence and (ii) a first target-hybridizing region hybridized to the first target sequence; the second probe comprises, from one end to another: (i) a second target-hybridizing region hybridized to the second target sequence, (ii) a barcode region corresponding to the target nucleic acid molecule or a sequence thereof, and (iii) a second splint-hybridizing region forming a second duplex with the second splint sequence; and the first duplex and the second duplex differ in stability. The first duplex may be more stable or less stable than the second duplex under the same condition or similar conditions.

In some embodiments, disclosed herein is a method for analyzing a sample, comprising forming a hybridization complex comprising a first probe, a second probe, a splint, and a target nucleic acid molecule in the sample, wherein: the target nucleic acid molecule comprises from 3' to 5' a first target sequence and a second target sequence; the splint comprises from 5' to 3' a first splint sequence and second splint sequence; the first probe comprises, from 5' to 3': (i) a first splint-hybridizing region forming a first duplex with the first splint sequence and (ii) a first target-hybridizing region hybridized to the first target sequence; the second probe comprises, from 5' to 3': (i) a second target-hybridizing region hybridized to the second target sequence, (ii) a barcode region corresponding to the target nucleic acid molecule or a sequence thereof (e.g., a sequence of interest, such as an SNP or point mutation), and (iii) a second splint-hybridizing region forming a second duplex with the second splint sequence. In some embodiments, the target nucleic acid molecule is a DNA, optionally a cDNA immobilized to one or more molecules in the sample and/or to a matrix embedding the sample, and the first and second probes and the splint are DNA molecules.

In some embodiments, the method further comprises ligating the first splint-hybridizing region and the second splint-hybridizing region, e.g., using enzymatic or chemical ligation and using the splint as template. In any of the preceding embodiments, the method may further comprise ligating the first target-hybridizing region and the second target-hybridizing region, e.g., using enzymatic or chemical ligation and using the target nucleic acid molecule as template. In some embodiments, the method may comprise generating a circular probe by (i) ligating the first target-hybridizing region and the second target-hybridizing region and (ii) ligating the first splint-hybridizing region and the second splint-hybridizing region.

In any of the preceding embodiments, the method may further comprise determining a sequence of the barcode region or complement thereof in the circular probe or an amplification product thereof, thereby detecting the target nucleic acid molecule in the sample.

In any of the preceding embodiments, the target nucleic acid molecule may comprise a cDNA or mRNA tethered to a three-dimensional (3D) matrix embedding the sample.

In any of the preceding embodiments, the first and/or second probes may not comprise one or more ribonucleotides. In any of the preceding embodiments, the first and/or second probes may not comprise a ribonucleotide at or near the 3' end. In any of the preceding embodiments, the 3' end nucleotide(s) of the first and/or second probes may not be a ribonucleotide. In any of the preceding embodiments, the first and/or second probes may be DNA probes.

In any of the preceding embodiments, forming the hybridization complex may comprise contacting the sample with the first probe and the second probe to allow probe hybridization to the target nucleic acid molecule. In any of the preceding embodiments, the method may comprise delivering the first probe and the second probe to the target nucleic acid molecule of the sample embedded in the 3D matrix, optionally wherein each of the first and second probes is no more than 100 nucleotides in length, optionally wherein each of the first and second probes is between about 30 and about 80 nucleotides in length. In any of the preceding embodiments, forming the hybridization complex may further comprise washing the sample after probe hybridization. In any of the preceding embodiments, forming the hybridization complex may further comprise contacting the sample with the splint to allow splint hybridization to the first and second probes hybridized to the target nucleic acid molecule. Alternatively, in any of the preceding embodiments, forming the hybridization complex may comprise contacting the sample with the first probe, the second probe, and the splint in one contacting step.

In any of the preceding embodiments, the first splint-hybridizing region and the first splint sequence can be complementary to each other. In any of the preceding embodiments, the second splint-hybridizing region and the second splint sequence can be complementary to each other.

In any of the preceding embodiments, the first duplex may be less stable than the second duplex. In some embodiments, hybridization of the first splint-hybridizing region to the first splint sequence can be more dynamic than hybridization of the second splint-hybridizing region to the second splint sequence. In some embodiments, hybridization of the second splint-hybridizing region to the second splint sequence can be more stable than hybridization of the first splint-hybridizing region to the first splint sequence.

Alternatively, in any of the preceding embodiments, the first duplex may be more stable than the second duplex. In any of the preceding embodiments, hybridization of the first splint-hybridizing region to the first splint sequence can be less dynamic than hybridization of the second splint-hybridizing region to the second splint sequence. In any of the preceding embodiments, hybridization of the second splint-hybridizing region to the second splint sequence can be less stable than hybridization of the first splint-hybridizing region to the first splint sequence.

In any of the preceding embodiments, the melting temperature of the first duplex can be at least 1° C., at least 2° C., at least 5° C., at least 10° C., or at least 15° C. higher than the melting temperature of the second duplex, or vice versa.

In any of the preceding embodiments, the first duplex can be at least 1, at least 2, at least 5, at least 10, or at least 15 base pairs longer than the second duplex, or vice versa. In any of the preceding embodiments, the first splint-hybridizing region can be 1, 2, 3, 4, 5, 6, 7, 8, 9, 10, 11, 12, 13, 14, 15, 16, 17, 18, 19, 20, or more nucleotides longer than the second splint-hybridizing region, or vice versa.

In any of the preceding embodiments, the first splint-hybridizing region can be at least 5 nucleotides and the second splint-hybridizing region can be shorter than 5 nucleotides in length. In any of the preceding embodiments, the first splint-hybridizing region can be at least 6 nucleotides and the second splint-hybridizing region can be shorter than 6 nucleotides in length. In any of the preceding embodiments, the first splint-hybridizing region can be at least 7 nucleotides and the second splint-hybridizing region can be shorter than 7 nucleotides in length. In any of the preceding embodiments, the first splint-hybridizing region can be at least 8 nucleotides and the second splint-hybridizing region can be shorter than 8 nucleotides in length.

In any of the preceding embodiments, the first splint-hybridizing region can be at least 9 nucleotides and the second splint-hybridizing region can be shorter than 9 nucleotides in length.

In any of the preceding embodiments, the first splint-hybridizing region can be at least 10 nucleotides and the second splint-hybridizing region can be shorter than 10 nucleotides in length. In any of the preceding embodiments, the first splint-hybridizing region can be 10, 11, 12, 13, 14, 15, 16, 17, 18, 19, 20, 21, 22, 23, 24, 25 or more nucleotides in length and the second splint-hybridizing region can be 1, 2, 3, 4, 5, 6, 7, 8, or 9 nucleotides in length.

In any of the preceding embodiments, the barcode region and the second splint-hybridizing region may not overlap. In some embodiments, the barcode region and the second splint-hybridizing region are connected by a phosphodiester bond. In some embodiments, the barcode region and the second splint-hybridizing region are connected by 1, 2, 3, 4, 5, 6, 7, 8, 9, 10 or more nucleotides.

Alternatively, in any of the preceding embodiments, the barcode region and the second splint-hybridizing region may partially or wholly overlap with each other. In some embodiments, the barcode region and the second splint-hybridizing region may partially overlap. In some embodiments, the barcode region and the second splint-hybridizing region may be the same region. In some embodiments, the barcode region may be within the second splint-hybridizing region, and in some alternative embodiments, the second splint-hybridizing region may be within the barcode region.

In any of the preceding embodiments, the barcode region can be between about 5 and about 25 nucleotides in length.

In any of the preceding embodiments, in the 5' to 3' or 3' to 5' direction, the second probe may comprise a common second splint-hybridizing region, the barcode region corresponding to the target nucleic acid molecule, an optional common linker region, and the second target-hybridizing region, where the common second splint-hybridizing region and the optional common linker region can be shared among a plurality of second probes each having a different second target-hybridizing region.

In any of the preceding embodiments, the first probe may not comprise a barcode region or a portion thereof. In any of the preceding embodiments, the first splint-hybridizing region may not comprise a barcode region or a portion thereof. In any of the preceding embodiments, the first splint-hybridizing region may comprise a common primer binding site shared among a plurality of first probes each hybridizing to a different first target sequence, and the primer binding site is not specific to a particular first target sequence. In any of the preceding embodiments, the first splint-hybridizing region may comprise a universal primer binding site shared among all of the first probes used in an assay for detecting a plurality of analytes in the sample, wherein each first probe is used to detect a different analyte and the primer binding site is not specific to a particular analyte. In any of the preceding embodiments, the free 5' or 3' nucleotide of the first splint-hybridizing region may not be part of a barcode region or a portion thereof corresponding to the target nucleic acid molecule. In any of the preceding embodiments, in the 5' to 3' or 3' to 5' direction, the first probe may consist of a common first splint-hybridizing region, an optional common linker region, and the first target-hybridizing region, where the common first splint-hybridizing region and the optional common linker region are shared among a plurality of first probes each having a different first target-hybridizing region.

In any of the preceding embodiments, determining the sequence of the barcode region can comprise performing sequencing by ligation using the splint or a portion thereof as primer.

In any of the preceding embodiments, the method may further comprise performing rolling circle amplification (RCA) using the splint or a portion thereof as primer and the circular probe as template to generate an RCA product of the circular probe. In any of the preceding embodiments, determining the sequence of a complement of the barcode region in the RCA product may comprise performing sequencing by ligation, sequencing by hybridization, and/or sequencing by synthesis.

In some embodiments, disclosed herein is a method for analyzing a sample, comprising: (a) reverse transcribing an RNA molecule in the sample to produce a cDNA molecule comprising a tethering moiety; (b) embedding the sample containing the cDNA molecule in a three-dimensional (3D) matrix, wherein the tethering moiety is configured to tether the cDNA molecule to the 3D matrix; (c) contacting the sample embedded in the 3D matrix with a first probe and a second probe, wherein: the first probe comprises, in the 5' to 3' direction: (i) a first splint-hybridizing region, (ii) a linker region, and (iii) a first target-hybridizing region that hybridizes to a first target sequence in the cDNA molecule, and the second probe comprises, in the 5' to 3' direction: (i) a second target-hybridizing region that hybridizes to a second target sequence in the cDNA molecule, (ii) a barcode region corresponding to the RNA molecule, and (iii) a second splint-hybridizing region; (d) contacting the sample embedded in the 3D matrix with a splint comprising a first splint sequence and second splint sequence, wherein the first splint sequence and the first splint-hybridizing region form a first duplex and the second splint sequence and the second splint-hybridizing region form a second duplex, and wherein the first duplex is more stable than the second duplex; (e) generating a circular probe hybridized to the cDNA molecule and the splint by (i) ligating the first target-hybridizing region and the second target-hybridizing region and (ii) ligating the first splint-hybridizing region and the second splint-hybridizing region; (f) generating a rolling circle amplification (RCA) product of the circular probe in the sample, wherein the RCA product comprises one or more modified nucleotides configured to tether the RCA product to the 3D matrix; and (g) sequencing a complement of the barcode region in the RCA product tethered to the 3D matrix, thereby detecting the RNA molecule in the sample. In some embodiments, the method further comprises clearing the sample embedded in the 3D matrix and degrading the RNA molecule between steps (b) and (c). In some embodiments, degrading the RNA molecule comprises contacting the sample embedded in the 3D matrix with RNase H. In some embodiments, the RCA product comprises multiple copies of a unit sequence comprising a complement of the linker region, and the method further comprises contacting the RCA product with one or more oligonucleotide probes that hybridize to complements of the linker region in different copies of the unit sequence. In some embodiments, the method further comprises ligating two ends of the one or more oligonucleotide probes hybridized different copies of the unit sequence in the RCA product.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 6 is a flow chart of an exemplary process for assembling and using an exemplary multicomponent probe. In some embodiments, the exemplary process comprises hybridizing a plurality of probe components to a target molecule, hybridizing a splint component to the probe components, filling a gap between the probes, and ligating the probe components together. In some embodiments, an amplification reaction can be performed. In some embodiments, the product of the amplification can be detected.

DETAILED DESCRIPTION

Figure 1:
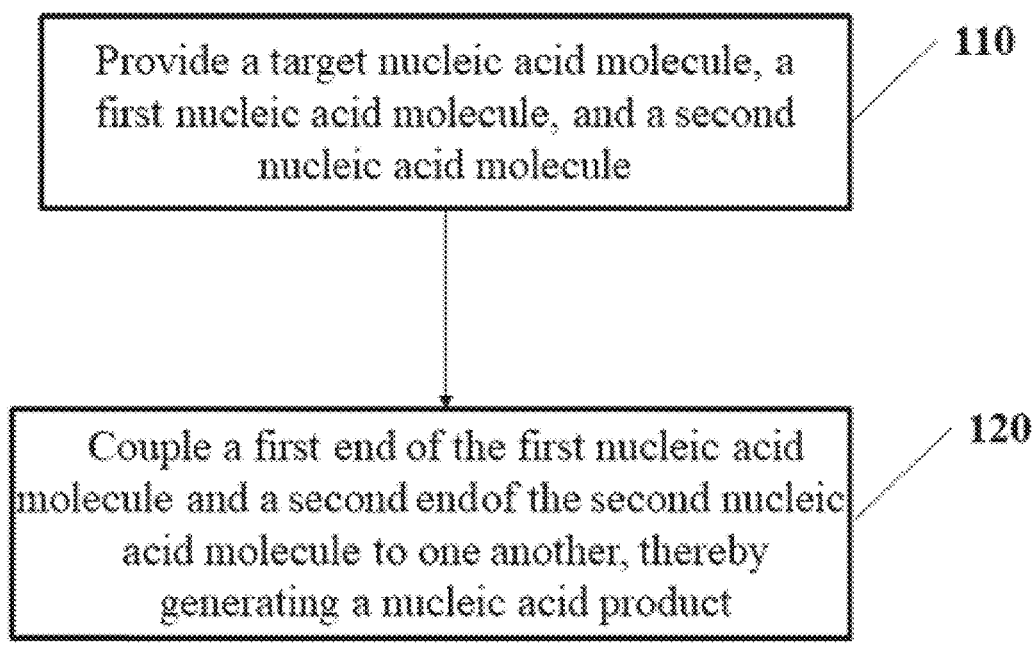
FIG. 1 is a flow chart of an exemplary process for nucleic acid analysis. In some embodiments, the exemplary process comprises providing a target nucleic acid molecule, a first nucleic acid molecule (e.g., a first probe) and a second nucleic acid molecule (e.g., a second probe). In some embodiments, the exemplary process comprises coupling a first end of the nucleic acid molecule and a second end of the second nucleic acid molecule to one another, thereby generating a nucleic acid product.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

I. Overview

In some embodiments, provided herein are methods and compositions for detecting RNA and/or DNA molecules in situ. In some embodiments, circularizable probes are hybridized to a target molecule (e.g., an RNA, cDNA, or genomic or mitochondrial DNA), circularized (e.g., by a ligase or chemical ligation), and amplified by rolling circle amplification (RCA), e.g., into a DNA nanoball, for detection by in situ sequencing and/or in situ sequential hybridization, including sequencing by hybridization, sequencing by ligation, sequencing by synthesis, sequencing by binding, and/or a method based on single molecule fluorescent in situ hybridization (smFISH).

In some embodiments, a method disclosed herein uses probes comprising terminal regions complementary to immediately adjacent regions on a target nucleic acid. In some embodiments, a method disclosed herein comprises hybridizing probes to the target nucleic acid at the complementary terminal regions; ligating the ends of the probes to form a circularized probe; subjecting the circularized probe to rolling circle amplification; and detecting the rolling circle amplification product. In some embodiments, a method disclosed herein uses probes comprising terminal regions complementary to regions on a target nucleic acid that are not immediately adjacent to one another. In some embodiments, a method disclosed herein comprises hybridizing the probes to the target nucleic acid at the complementary terminal regions; extending one or more ends of the probes, such as by a polymerase and/or a ligase reaction (nucleotides may be added base by base or as an oligonucleotide), until the ends are immediately adjacent; ligating the ends of the probes to form a circularized probe; subjecting the circularized probe to rolling circle amplification; and detecting the rolling circle amplification product. In some embodiments, the probes form a probe pair, which can also be referred to as a multicomponent probe.

In some embodiments, a multicomponent probe herein comprises at least two regions complementary to a target molecule. In some embodiments, the at least two regions can independently be between about 10 and about 40 bases long. In some embodiments, the at least two regions can be equal in length. Alternatively, in some embodiments, the at least two regions can be different in length. In some embodiments, each component of the multicomponent probe herein comprises a "backbone" segment that can be connected to a "backbone" segment of the other component in order to connect terminal target-complementary regions. In some embodiments, the "backbone" segment may comprise one or more nucleic acid sequence domains, such as RCA primer binding site and/or sequencing primer binding sites, and barcode or detection domains, such as barcodes for sequencing-by-synthesis, sequencing-by-ligation, or sequencing-by-hybridization. In some embodiments, the total length of a multicomponent probe herein can be between about 60 and about 160 bases long.

In some embodiments, provided herein is a probe architecture comprising multiple probe components ("multicomponent probe"), comprising: a first probe component complementary to a target molecule; a second probe component complementary to the target molecule; and a splint component. In some embodiments, the splint is a backbone splint that hybridizes to the first and/or second probes at a region that does not overlap with the target-hybridizing regions and does not overlap with the barcode region(s) of the probes. In some embodiments, the splint serves as a primer for RCA, and may comprise features for optimal RCA priming, such as a modified 3' end resistant to 3'→5' exonuclease activity of Phi29 DNA polymerase. In some embodiments, an RCA primer separate from the splint can be used. The splint and/or the separate RCA primer can comprise one or more phosphorothioate linkages (e.g., 3' thiophosphate-protected), thereby protecting the polynucleotide from 3'→5' exonuclease degradation by the polymerase while allowing priming by the polymerase.

In some embodiments, provided herein is a method comprising a one-step multicomponent assembly process in which the first and second probe components and the splint component are added to the target molecule in one step. In some embodiments, under a target-binding reaction condition, the splint hybridizes to neither or one of the first and second probe components comprising target-complementary, but under the target-binding reaction condition, the splint does not form a stable hybridization to both the first and second probe components. If the splint formed a stable hybridization to both the first and second probe components, in a mixture containing a plurality of probes targeting different target molecules, this may result in the formation of complexes wherein the splint could hybridize to two probe components that are not complementary to the same target molecule or sequence, resulting in a "chimeric" structure which is incapable of hybridizing to a target nucleic acid in a manner that would enable closure of the circle (with or without a gap) at the junction of the ends. In some embodiments, to reduce the formation of the "chimeric" structure, provided herein is a splint capable of hybridizing to one or both probe components under the same reaction conditions (e.g., the same condition for probe hybridization to a target nucleic acid) in a dynamic manner, where the probe components can be connected by a ligase.

In some embodiments, to reduce the formation of the "chimeric" structure, provided herein is a splint capable of hybridizing to one or both probe components under a different reaction condition (e.g., different from the condition for probe hybridization to a target nucleic acid) in a dynamic or stable manner, where the probe components can be connected by a ligase. In some embodiments, the domain of splint-complementarity to the second probe component is shorter or has reduced melting temperature compared to the domain of splint-complementarity to the first probe component. In some embodiments, the splint and the second probe component hybridize at a sequence that is sufficiently long to facilitate ligation of the first and second probe components. In some embodiments, the sufficiently long sequence is 1, 2, 3, 4, 5, 6, 7, 8, 9, 10, 11, 12, or more nucleotides in length. In some embodiments, the splint is configured such that it dynamically hybridizes to the second probe component. In some embodiments, "dynamic hybridization" means that at the equilibrium under a reaction condition, less than about 1%, less than about 5%, less than about 10%, less than about 20%, less than about 30%, less than about 40%, less than about 50%, less than about 60%, less than about 70%, less than about 80%, or less than about 90% of the splint molecules are bound to the corresponding second probe molecules, and/or less than about 1%, less than about 5%, less than about 10%, less than about 20%, less than about 30%, less than about 40%, less than about 50%, less than about 60%, less than about 70%, less than about 80%, or less than about 90% of the second probe molecules are bound to the corresponding splint molecules. In some embodiments, the equilibrium splint-second probe bound (hybridized) fraction is low under the reaction condition. In some embodiments, individual complexes with a first probe and a second probe hybridized to the target nucleic acid molecule in proximity have the first probe that is dynamically annealing and melting to the second probe.

In some embodiments, provided herein is a method comprising a two-step multicomponent assembly process in which the first and second probe components are contacted with a target molecule and allowed to pre-hybridize to the target molecule, and the splint component is then added. In some embodiments, the splint may dynamically hybridize to both probe components, where the target-complementary sequences of the probe components are already pre-hybridized to the target molecule. In some embodiments, the splint component binds to the free ends of both probe components and excess components can be washed from the sample.

In some embodiments, the first probe or the second probe alone is not competent for detection in the event of self-circularization, such as for detection by sequencing by ligation or synthesis, where the sequencing primer domain is on one component and the barcode domain is on a separate component. In some embodiments, when one component comprises the domains necessary and sufficient for detection, a method disclosed herein may still reduce the false positive rate by reducing the length of that component to reduce the rate of self-circularization, since longer nucleic acid molecules are more prone to self-circularization.

In some embodiments, the target molecule is an RNA or a DNA reverse transcribed from an RNA. In some embodiments, the target molecule or derivative thereof is contacted with two probe components, wherein the probe components separately hybridize to the target molecule. In some embodiments, the sample is contacted with splint component to ligate backbone regions of the probe components (e.g., regions that do not hybridize to the target molecule). The sample can be optionally contacted with a DNA- or RNA-dependent polymerase, or ligase with gap-fill oligonucleotides, to close a gap between the first and second probes hybridized to the target molecule and/or close a gap between the splint-complementary components hybridized to the splint. In some embodiments, the sample is contacted with one or more ligase(s), such as a DNA ligase, or in the case of an RNA target, a ligase capable of ligating a hybrid duplex, such as SplintR®. In some embodiments, a DNA ligase can be used to close the nicks at the template and within the probe backbone. In some embodiments, the circularized product of the probe components can be detected and/or used a template for rolling circle amplification which can be detected.

In some embodiments, disclosed herein is a method comprising hybridizing the first and second probes in one step, hybridizing the splint component in a second step, and conducting each of the enzyme reactions (e.g., gap-filling and/or nick ligation) in separate steps. In some embodiments, disclosed herein is a method comprising hybridizing all components (e.g., the first and second probe components and the splint component) in a single step, and conducting each of the enzyme reactions (e.g., gap-filling and/or nick ligation) in separate steps. In some embodiments, disclosed herein is a method comprising hybridizing all components (e.g., the first and second probe components and the splint component) in a single step, conducting the enzyme reactions (e.g., gap-filling and/or nick ligation) in one step, and conducting RCA and detection in separate steps. In some embodiments, disclosed herein is a method comprising hybridizing all components (e.g., the first and second probe components and the splint component) in the same reaction as the enzyme reactions (e.g., gap-filling and/or nick ligation), conducting the hybridization and enzyme reactions in one step, and conducting RCA and detection in separate steps.

The methods and compositions disclosed here may provide one or more advantages over existing methods.

In some embodiments, a method disclosed herein reduces false positive rates. While most DNA ligases used for padlock probe formation or circularization prefer to ligate a duplex DNA, most DNA ligases have a certain activity for ssDNA ligation including self-circularization, and self-circularization reactions are thought to be more favorable for longer DNA species due to considerations like persistence length, wherein the ends of a longer DNA species act more like ends of two separate DNA molecules for ligation in terms of molecular tension and steric effects, but with a high effective concentration due to the physical proximity of the ends belonging to the same molecule, wherein the ligation reaction being an enzymatic reaction the kinetics are dependent on concentration. See Kuhn et al., Template-independent ligation of single-stranded DNA by T4 DNA ligase, *The FEBS Journal* 272.23 (2005): 5991-6000. Therefore, padlock probes are expected to self-circularize at a certain rate. Self-circularized padlock probes, bearing the backbone or other features required for detection, such as for a sequencing by ligation method, having a sequencing primer domain and a barcode domain, are competent for detection. Target- or template-independent self-circularization of padlock probes can create false positive signals for molecular detection.

In some embodiments, the two components of the multicomponent probe assembly are brought into proximity by hybridization to the target molecule in order to enable the ligation and circularization at both the target-cognate nick (with or without gap filling) and the nick formed in the backbone. In certain embodiments, RCA products formed by self-circularization of either component are not competent for detection, e.g., by sequencing. In certain embodiments, self-circularization of the first probe or the second probe is reduced using a method disclosed herein.

In some embodiments, a method disclosed herein results in faster reaction time. In some embodiments, diffusion kinetics for nucleic acid such as DNA within a porous 3D matrix can have a linear dependency on several features of the nucleic acid, including the molecular weight, strandedness (e.g., ssDNA versus dsDNA) or partial secondary structure, and the "size" of the molecule, such as determined by the average persistence length of unstructured single-stranded or double-stranded DNA polymers. In some aspects, longer nucleic acid such as DNA species diffuses more slowly through a 3D matrix than shorter nucleic acid such as DNA species.

For instance, dividing a padlock probe into separate components, which are circularized at both the backbone and cognate to the target, can enable faster diffusion kinetics of probe components within a 3D matrix, wherein each component is shorter than if a padlock probe were used. In some embodiments, faster diffusion may help shorten time required for hybridization since hybridization reaction kinetics can be limited by diffusion. In some embodiments, faster diffusion may help shorten time required for effective washing, since rate of washing excess unbound probes from the 3D matrix may be limited by diffusion as well.

In some embodiments, a method disclosed herein requires fewer probes for multiplex detection of sequence variants. For instance, for detection of sequence variation, including insertions, deletions, SNP/SNV, alternative splicing, and RNA editing, a single component of the assembly may be complementary to a conserved domain among the set of variants, and a plurality of second components specific to each of the variants being detected, wherein the second component comprises the sequence-specific detection feature such as a barcode sequence.

In some embodiments, a method disclosed herein results in higher quality of the probes used for detection, e.g., circular or circularizable probes assembled from shorter probe components may contain fewer errors compared to long padlock probes synthesized as a whole. Chemical DNA synthesis methods, including of padlock probes, have an intrinsic error rate which is proportional to the length of the oligonucleotide, where a population of longer DNA species may have a higher fraction of molecules containing an error relative to a designed sequence. Generally, populations of shorter probes are expected to contain fewer molecules with sequence errors compared to longer probes. For instance, chemical synthesis that proceeds in the 3'→5' direction may produce oligonucleotides that contain more synthesis errors at the 5' end. In some embodiments, the 5' end of a padlock probe assembled from shorter probe components may contain fewer errors compared to the 5' end of a long padlock probe synthesized using base-by-base chemical synthesis.

II. Methods and Compositions for Sample Analysis

In an aspect, the present disclosure provides a composition for sample analysis, including analysis of nucleic acid (e.g., mRNA or cDNA) and/or non-nucleic acid analytes (e.g., proteins) in situ in sample. The composition may comprise a first nucleic acid molecule comprising (i) a first hybridizing region having a first sequence complementary to a first target sequence of a target nucleic acid molecule and (ii) a first nonhybridizing region at a first end of the first nucleic acid molecule. The composition may comprise a second nucleic acid molecule comprising (i) a second hybridizing region having a second sequence complementary to a second target sequence of the target nucleic acid molecule and (ii) a second nonhybridizing region at a second end of the second nucleic acid molecule. The first nucleic acid molecule and the second molecule may be configured such that, upon hybridization of the first sequence to the first target sequence and the second sequence to the second target sequence: (1) the first nonhybridizing region and the second nonhybridizing region do not hybridize with the target nucleic acid molecule; and (2) the first end and the second end undergo coupling to one another.

The first nucleic acid molecule and the second nucleic acid molecule may be configured such that, upon hybridization of the first sequence to the first target sequence and the second sequence to the second target sequence, the first end and the second end undergo coupling to one another via a nucleic acid extension reaction. The nucleic acid extension reaction may comprise the use of a polymerase. Non-limiting examples of polymerases may be described elsewhere herein. For example, the polymerase can add bases to fill a gap between the first and second nucleic acid molecules. The nucleic acid extension reaction may comprise binding an additional nucleic acid molecule between the first and second nucleic acid molecules. The additional nucleic acid molecule may be configured to be a template. For example, the additional nucleic acid molecule can be a template for the addition of the nucleotides during the nucleic acid extension reaction. The additional nucleic acid molecule may be a third nucleic acid molecule as described elsewhere herein. The additional nucleic acid molecule may be the target nucleic acid molecule. For example, the first end and the second end can both be hybridized to the third nucleic acid molecule, and the third nucleic acid molecule can be the template for the nucleic acid extension coupling reaction.

The first nucleic acid molecule and the second nucleic acid molecule may be configured such that, upon hybridization of the first sequence to the first target sequence and the second sequence to the second target sequence, the first end and the second end undergo coupling to one another via a nucleic acid ligation reaction. The nucleic acid ligation reaction may comprise the use of a ligase enzyme. The ligase enzyme may be, for example, DNA ligase I, DNA ligase II, DNA ligase III, DNA ligase IV, *E. coli* DNA ligase, T4 DNA ligase, Taq ligase, SplinR ligase, or the like. The nucleic acid ligation reaction may comprise a nick repair. The nucleic acid ligation reaction may be a ligation of two adjacent nucleic acid molecules, for example, the first and second nucleic acid molecules can be separated by 0 bases (e.g., adjacent) and a ligase (e.g., a DNA ligase) can ligate the first and second nucleic acid molecules together. The nucleic acid ligation reaction may be a blunt end ligation reaction, a sticky end ligation reaction, nick ligation, or the like.

The first nucleic acid molecule and the second nucleic acid molecule may be configured such that, upon hybridization of the first sequence to the first target sequence and the second sequence to the second target sequence, the first end and the second end undergo coupling to one another via a hybridization reaction. The hybridization reaction may comprise the introduction of an oligonucleotide to bridge a gap between the first and second nucleic acid molecules. For example, if the first and second ends are bound to another nucleic acid molecule with a 5-nucleotide gap between them, a 5-nucleotide oligonucleotide can be hybridized into the gap. The hybridization reaction may comprise hybridizing a plurality of oligonucleotides between the first and second ends of the first and second nucleic acid molecules. For example, a gap between the first and second ends of 6 nucleotides can be hybridized with two 3-nucleotide oligonucleotides.

The first nucleic acid molecule and the second nucleic acid molecule may be configured such that, upon hybridization of the first sequence to the first target sequence and the second sequence to the second target sequence, the first end and the second end undergo coupling to one another via a nucleic acid extension and a nucleic acid ligation reaction. For example, a polymerase can extend the first end to be adjacent to the second end, and a ligase can bind the newly adjacent first and second ends together. The first nucleic acid molecule and the second nucleic acid molecule may be configured such that, upon hybridization of the first sequence to the first target sequence and the second sequence to the second target sequence, the first end and the second end undergo coupling to one another via a hybridization reaction and a nucleic acid ligation reaction. For example, an oligonucleotide can bridge a gap between the first and the second ends, and a ligase can bind the first and second ends to the oligonucleotide, thus coupling the first and second ends.

The first nucleic acid molecule and the second nucleic acid molecule may be configured such that, upon hybridization of the first sequence to the first target sequence and the second sequence to the second target sequence, the first end of the first nucleic acid molecule and the second end of the second nucleic acid molecule may be adjacent. For example, the first sequence may be configured to hybridize to a sequence on the target nucleic acid molecule adjacent to the sequence of the target nucleic acid molecule the second sequence is configured to hybridize to. In this example, the first and second nucleic acid molecules are the same length, so the first end and the second end are adjacent. The first nucleic acid molecule and the second nucleic acid molecule may be configured such that, upon hybridization of the first sequence to the first target sequence and the second sequence to the second target sequence, the first end of the first nucleic acid molecule and the second end of the second nucleic acid molecule may be separated by a gap of at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The first nucleic acid molecule and the second nucleic acid molecule may be configured such that, upon hybridization of the first sequence to the first target sequence and the second sequence to the second target sequence, the first end of the first nucleic acid molecule and the second end of the second nucleic acid molecule may be separated by a gap of at most about 50, 45, 40, 35, 30, 25, 20, 19, 18, 17, 16, 15, 14, 13, 12, 11, 10, 9, 8, 7, 6, 5, 4, 3, 2, or fewer nucleotides. The first nucleic acid molecule and the second nucleic acid molecule may be configured such that, upon hybridization of the first sequence to the first target sequence and the second sequence to the second target sequence, the opposite end of the first nucleic acid molecule and the opposite end of the second nucleic acid molecule may be adjacent. The first nucleic acid molecule and the second nucleic acid molecule may be configured such that, upon hybridization of the first sequence to the first target sequence and the second sequence to the second target sequence, the opposite end of the first nucleic acid molecule and the opposite end of the second nucleic acid molecule may be separated by a gap of at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The first nucleic acid molecule and the second nucleic acid molecule may be configured such that, upon hybridization of the first sequence to the first target sequence and the second sequence to the second target sequence, the opposite end of the first nucleic acid molecule and the opposite end of the second nucleic acid molecule may be separated by a gap of at most about 50, 45, 40, 35, 30, 25, 20, 19, 18, 17, 16, 15, 14, 13, 12, 11, 10, 9, 8, 7, 6, 5, 4, 3, 2, or fewer nucleotides.

The composition may comprise a third nucleic acid molecule (e.g., a splint) which can be a molecule separate from the target nucleic acid molecule. A sequence of the third nucleic acid molecule may be complementary to at least a portion of the first nonhybridizing region. For example, a portion of the third nucleic acid molecule can be configured to hybridize to a terminal portion of the first nonhybridizing region. The sequence may comprise at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The sequence may comprise at most about 50, 45, 40, 35, 30, 25, 20, 19, 18, 17, 16, 15, 14, 13, 12, 11, 10, 9, 8, 7, 6, 5, 4, 3, 2, or fewer nucleotides. The sequence may be hybridized with the at least the portion of the first nonhybridizing region. For example, the third nucleic acid molecule (e.g., the splint) can be hybridized to the first nonhybridizing region (e.g., the first splint-hybridizing region) via the sequence (e.g., the first splint sequence). An additional sequence (e.g., the second splint sequence) of the third nucleic acid molecule may be complementary to at least a portion of the second nonhybridizing region (e.g., the second splint-hybridizing region). For example, the portion of the third nucleic acid molecule corresponding to the additional sequence can be configured to hybridize to at least a portion of the second nonhybridizing region. The additional sequence may comprise at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The additional sequence may comprise at most about 50, 45, 40, 35, 30, 25, 20, 19, 18, 17, 16, 15, 14, 13, 12, 11, 10, 9, 8, 7, 6, 5, 4, 3, 2, or fewer nucleotides. The additional sequence may be configured to have a lower melting temperature than that of the sequence to allow for dynamic binding. In some embodiments, the second nonhybridizing region binds to the additional sequence with a melting temperature of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 degrees Celsius less than the melting temperature between the first nonhybridizing region and the sequence. In some embodiments, the second nonhybridizing region binds to the additional sequence with a melting temperature that is between about 1 and 50, 1 and 45, 1 and 40, 1 and 35, 1 and 30, 1 and 25, 1 and 20, 1 and 15, 1 and 15, 1 and 10, 1 and 5, 5 and 50, 5 and 45, 5 and 40, 5 and 35, 5 and 30, 5 and 25, 5 and 20, 5 and 15, 5 and 10, 10 and 50, 10 and 45, 10 and 40, 10 and 35, 10 and 30, 10 and 25, 10 and 20, 10 and 15, 15 and 50, 15 and 45, 15 and 40, 15 and 35, 15 and 30, 15 and 25, 15 and 20, 20 and 50, 20 and 45, 20 and 40, 20 and 35, 20 and 30, 20 and 25, 25 and 50, 25 and 45, 25 and 40, 25 and 35, 25 and 30, 30 and 50, 30 and 45, 30 and 40, 30 and 35, 35 and 50, 35 and 45, 35 and 40, 40 and 50, 40 and 45, or 45 and 50 degrees Celsius less than the melting temperature the sequence binds to the first nonhybridizing region. The additional sequence may be configured to have a lower affinity for the second nonhybridizing region than the sequence has for the first nonhybridizing region. In some embodiments herein, the additional sequence may bind to the second nonhybridizing region more dynamically than the binding between the sequence and the first nonhybridizing sequence. The additional sequence may be shorter than the sequence, comprise fewer cytosine and/or guanine nucleotides, or the like, or any combination thereof. In some embodiments, the additional sequence binding to the second nonhybridizing region is at least 1, 2, 3, 4, 5, 6, 7, 8, 9, 10, 11, 12, 13, 14, 15, 16, 17, 18, 19, 20, 25, 30, 35, 40, 45, 50, or fewer nucleotides than the sequence binding to the first nonhybridizing region. Alternatively, in some aspects, the additional sequence binding to the second nonhybridizing region may be about 5%, 10%, 15%, 20%, 25%, 30%, 35%, 40%, 45%, 50%, 55%, 60%, 65%, 70%, 75%, 80%, 85%, 90%, 95%, 100% shorter than sequence binding to the first nonhybridizing region. In some embodiments, the portion of the additional sequence binding to the second nonhybridizing region may contain at least 1, 2, 3, 4, 5, 6, 7, 8, 9, 10, 11, 12, 13, 14, 15, 16, 17, 18, 19, 20, 25, 30, 35, 40, 45, 50 or fewer G or C nucleotides than the sequence binding to the first nonhybridizing region. In some embodiments, the portion of the additional sequence binding to the second nonhybridizing region may contain between 1 and 50, 1 and 45, 1 and 40, 1 and 35, 1 and 30, 1 and 25, 1 and 20, 1 and 15, 1 and 15, 1 and 10, 1 and 5, 5 and 50, 5 and 45, 5 and 40, 5 and 35, 5 and 30, 5 and 25, 5 and 20, 5 and 15, 5 and 10, 10 and 50, 10 and 45, 10 and 40, 10 and 35, 10 and 30, 10 and 25, 10 and 20, 10 and 15, 15 and 50, 15 and 45, 15 and 40, 15 and 35, 15 and 30, 15 and 25, 15 and 20, 20 and 50, 20 and 45, 20 and 40, 20 and 35, 20 and 30, 20 and 25, 25 and 50, 25 and 45, 25 and 40, 25 and 35, 25 and 30, 30 and 50, 30 and 45, 30 and 40, 30 and 35, 35 and 50, 35 and 45, 35 and 40, 40 and 50, 40 and 45, or 45 and 50 fewer G/C nucleotides than the sequence binding to the first nonhybridizing region. In alternative embodiments, the additional sequence binding to the second nonhybridizing region may have about 5%, 10%, 15%, 20%, 25%, 30%, 35%, 40%, 45%, 50%, 55%, 60%, 65%, 70%, 75%, 80%, 85%, 90%, 95% or 100% lower GC content than the sequence binding to the first nonhybridizing region. The difference in melting temperature may relate to a bound/unbound equilibrium of the third nucleic acid molecule. For example, conditions can be created such that the binding of the sequence to the first nonhybridizing region is stable while the binding of the additional sequence to the second nonhybridizing region is dynamic. In this example, the dynamic binding can be under a given reaction condition such as a buffer composition including monovalent and divalent cation salts and under a given reaction temperature or temperature program (e.g., held at 45° C. for 2 hours and then held at 37° C. for 2 hours). In some embodiments, the hybridization of third nucleic acid molecule (e.g., the splint) to the first nonhybridizing region (e.g., the first splint-hybridizing region) can be performed in a different condition (e.g., buffer) compared to the circularization of the first and second probes.

The additional sequence may be hybridized with the at least the portion of the second nonhybridizing region. The sequence may be hybridized with the at least the portion of the first nonhybridizing region and the additional sequence can be hybridized to the at least the portion of the second nonhybridizing region. For example, the third nucleic acid (e.g., the splint) can be hybridized to both the first nucleic acid and the second nucleic acid simultaneously. Alternatively, the third nucleic acid (e.g., the splint) can be hybridized to the first nucleic acid and then to the second nucleic acid, or vice versa. The third nucleic acid may hybridize to the first nonhybridizing region faster than to the second nonhybridizing region, or vice versa. The third nucleic acid may hybridize to the first nonhybridizing region more stably than to the second nonhybridizing region, or vice versa. The third nucleic acid molecule may hold the first and second nucleic acid molecules adjacent to each other. The third nucleic acid molecule may be a primer for an enzyme. The enzyme may be a polymerase, a ligase, or the like. For example, the third nucleic acid molecule can be a primer for a polymerase enzyme. A third end of the third nucleic acid molecule may comprise an exonuclease-resistant moiety. The exonuclease-resistant moiety may be one or more phosphorothioate linkages, 2'-O-methly modifications, 2'-fluoro modifications, inverted dT or ddT modifications, phosphorlyation modifications, C3 spacers, or the like.

The third nucleic acid molecule may comprise a primer sequence configured for nucleic acid amplification. The primer may be a DNA primer. The primer may be an RNA primer. The primer may be configured as a binding site, an activating site, or the like, or any combination thereof for a polymerase. Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. The primer sequence may be configured for rolling circle amplification. For example, the primer may be a primer for a polymerase configured for rolling circle amplification. The rolling circle amplification may generate a concatemer comprising a plurality of repeats of the sequence of the target nucleic acid.

The composition may comprise the target nucleic acid molecule. The first sequence of the first nucleic acid molecule may be hybridized to the first target sequence of the target nucleic acid molecule. The second sequence of the second target nucleic acid may be hybridized with the second target sequence. The target nucleic acid molecule may be complementary deoxyribonucleic acid (cDNA) derived from reverse transcribed ribonucleic acid (RNA). The reverse transcription may be performed with the aid of a reverse transcriptase. The reverse transcriptase may be a retroviral reverse transcriptase (e.g., HIV-1 reverse transcriptase, M-MLV reverse transcriptase, AMV reverse transcriptase), a human derived reverse transcriptase (e.g., telomerase reverse transcriptase), or the like. The target nucleic acid may be a messenger ribonucleic acid (mRNA) molecule. The target nucleic acid molecule may be an analyte as described elsewhere herein. The target nucleic acid molecule may be derived from a subject. The target nucleic acid molecule may be a genomic nucleic acid molecule. For example, the target nucleic acid molecule can be a portion of a genome of a subject. The composition may comprise a three-dimensional (3D) matrix. The 3D matrix may be a 3D matrix as described elsewhere herein. The target nucleic acid molecule may be immobilized to the 3D matrix. The immobilization may be a reversable immobilization (e.g., immobilized via hybridization) or irreversible immobilization (e.g., immobilized via chemical bonds).

The first hybridizing region may be at a first opposite end of the first nucleic acid molecule from the first nonhybridizing region. The second hybridizing region may be at a second opposite end of the second nucleic acid molecule from the second nonhybridizing region. For example, the hybridizing region can be connected directly to the nonhybridizing region if the nucleic acid molecule does not have any other regions. In another example, the hybridizing region can be connected by one or more additional regions to the nonhybridizing region. The first nucleic acid molecule and the second nucleic acid molecule may be configured such that, upon hybridization of the first sequence to the first target sequence and the second sequence to the second target sequence, the first opposite end and the second opposite end may undergo coupling to one another via a nucleic acid extension reaction. The nucleic acid extension reaction may be a nucleic acid extension reaction as described elsewhere herein. The first nucleic acid molecule and the second nucleic acid molecule may be configured such that, upon hybridization of the first sequence to the first target sequence and the second sequence to the second target sequence, the first opposite end and the second opposite end may undergo coupling to one another via a nucleic acid ligation reaction. The nucleic acid ligation reaction may be a ligation reaction as described elsewhere herein. The first nucleic acid molecule and the second nucleic acid molecule may be configured such that, upon hybridization of the first sequence to the first target sequence and the second sequence to the second target sequence, the first opposite end and the second opposite end may undergo coupling to one another via a hybridization reaction. The hybridization reaction may be a hybridization reaction as described elsewhere herein. The first nucleic acid molecule and the second nucleic acid molecule may be configured such that, upon hybridization of the first sequence to the first target sequence and the second sequence to the second target sequence, the first opposite end and the second opposite end may undergo coupling to one another via a nucleic acid extension reaction and a nucleic acid ligation reaction. The first nucleic acid molecule and the second nucleic acid molecule may be configured such that, upon hybridization of the first sequence to the first target sequence and the second sequence to the second target sequence, the first opposite end and the second opposite end may undergo coupling to one another via a hybridization reaction and a nucleic acid ligation reaction.

The first nonhybridizing region of the first nucleic acid molecule may not have a sequence complementary to the first target sequence. For example, the first nonhybridizing region may be configured to not hybridize to the first target sequence. The second nonhybridizing region may not have a sequence complementary to the second target sequence. The first nucleic acid molecule may comprise a sequencing primer binding site. For example, the first nucleic acid can comprise a sequencing primer binding site as the first nonhybridizing region. The second nucleic acid molecule may comprise a barcode domain. For example, the second nucleic acid molecule can comprise a barcode domain as the second nonhybridizing region. The barcode domain may be configured to bind to a labeled probe as described elsewhere herein. The second nucleic acid molecule may comprise a sequencing primer binding site. The first nucleic acid molecule may comprise a barcode domain. The first nucleic acid molecule (e.g., the first probe) in a hybridization complex disclosed herein may comprise both a sequencing primer binding site and a barcode domain, whereas the second nucleic acid molecule (e.g., the second probe) in the hybridization complex does not comprise a barcode domain or portion thereof. Likewise, the second nucleic acid molecule (e.g., the second probe) in a hybridization complex may comprise both a sequencing primer binding site and a barcode domain, whereas the first nucleic acid molecule (e.g., the first probe) in the hybridization complex does not comprise a barcode domain or portion thereof. In some embodiments, a barcode domain can be in one of the first and second probes but not in both probes. In some embodiments, the sequencing primer binding site and the barcode domain are substantially on separate components (e.g., the sequencing primer binding site on the first probe and the barcode domain on the second probe). In some embodiments, there is no barcode region or portion thereof in the first splint-hybridizing region and/or the second splint-hybridizing region. In some embodiments, the free 5' or 3' nucleotide of the first or second splint-hybridizing region may not be part of any barcode region or portion thereof.

In another aspect, the present disclosure provides a method for analyzing a target nucleic acid molecule. The method may comprise providing the target nucleic acid molecule, a first nucleic acid molecule, and a second nucleic acid molecule. The first nucleic acid molecule may comprise a first hybridizing region having a first sequence hybridized to a first target sequence of a target nucleic acid molecule and a first nonhybridizing region at a first end of the first nucleic acid molecule that is not hybridized with the target nucleic acid molecule. The second nucleic acid molecule may comprise a second hybridizing region hybridized to a second target sequence of the target nucleic acid molecule and a second nonhybridizing region at a second end of the second nucleic acid molecule that is not hybridized with the target nucleic acid molecule. The first end and the second end may be coupled to one another, thereby generating a nucleic acid product.

FIG. 1 is a flow chart of an exemplary process for nucleic acid analysis. In an operation 110, the process 100 may comprise providing a target nucleic acid molecule, a first nucleic acid molecule, and a second nucleic acid molecule. The first nucleic acid may comprise a first hybridizing region. The first hybridizing region may have a first sequence hybridized to a first target sequence of the target nucleic acid molecule. The first nucleic acid may comprise a first nonhybridizing region at a first end of the first nucleic acid molecule. The first nonhybridizing region may not be hybridized with the target nucleic acid molecule. The second nucleic acid molecule may comprise a second hybridizing region. The second hybridizing region may be hybridized to a second target sequence of the target nucleic acid molecule. The second nucleic acid molecule may comprise a second nonhybridizing region at a second end of the second nucleic acid molecule. The second non hybridizing region may not be hybridized with the target nucleic acid molecule.

The target nucleic acid molecule may be an analyte as described elsewhere herein. The target nucleic acid molecule may be a ribonucleic acid (RNA), a single stranded deoxyribonucleic acid (ssDNA), or a double stranded deoxyribonucleic acid (dDNA). The target nucleic acid molecule may be complementary deoxyribonucleic acid (cDNA). The cDNA may be derived from a reverse transcribed ribonucleic acid. For example, a ribonucleic acid as described elsewhere herein such as, for example, a messenger RNA, can be reverse transcribed to generate a cDNA strand. The target nucleic acid molecule may be an RNA selected from the group consisting of messenger RNA (mRNA), ribosomal RNA (rRNA), transfer RNA (tRNA), microRNA (miRNA), small cytoplasmic RNA (scRNA), and small nuclear RNA (snRNA). The target nucleic acid molecule may be a messenger RNA molecule. The target nucleic acid molecule may be a genomic nucleic acid molecule (e.g., DNA held within the nucleus of a cell). The target nucleic acid molecule may be derived from a genomic nucleic acid molecule (e.g., a genomic DNA molecule fragmented to form the target nucleic acid molecule). For example, the target nucleic acid molecule can be a portion of fragmented chromosomal DNA. The target nucleic acid molecule may be immobilized to a three-dimensional (3D) matrix as described elsewhere herein.

The first nonhybridizing region may not have a sequence complementary to the first target sequence. The first nonhybridizing region may comprise a functional domain. The functional domain may be a sequencing primer domain (e.g., a sequence that can serve as a polymerase primer binding site), a barcoding domain (e.g., a domain of a predetermined sequence that can be configured to identify other sequences bound to it), or the like, or any combination thereof. The first nonhybridizing region may be connected to the first hybridizing region via one or more additional regions. For example, a region configured as a barcoding region can be between the first hybridizing region and the first nonhybridizing region. The second nonhybridizing region may not have a sequence complementary to the second target sequence. The second nonhybridizing region may comprise a functional domain. The functional domain may be a sequencing primer domain (e.g., a sequence that can serve as a polymerase primer binding site), a barcoding domain (e.g., a domain of a predetermined sequence that can be configured to identify other sequences bound to it), or the like, or any combination thereof. The second nonhybridizing region may be connected to the second hybridizing region via one or more additional regions. For example, a region configured as a barcoding region can be between the second hybridizing region and the second nonhybridizing region.

The first nucleic acid molecule may comprise a sequencing primer binding site. The sequencing primer binding site may be a binding site configured to bind to polymerases as described elsewhere herein (e.g., Phi29 DNA polymerase). The second nucleic acid molecule may comprise a barcode domain. The barcode domain may be a plurality of bases configured in a predetermined order. The predetermined order may enable the identification of the barcode domain, and other domains linked to the barcode domain. For example, binding an oligonucleotide comprising a fluorescent moiety to a barcode domain can enable an optical detection of the barcode domain and a determination of the presence of a target nucleic acid sequence associated with the barcode domain. The second nucleic acid molecule may comprise a sequencing primer binding site. The first nucleic acid molecule may comprise a barcode domain. The first nucleic acid molecule may comprise both a sequencing primer binding site and a barcode domain. The second nucleic acid molecule may comprise both a sequencing primer binding site and a barcode domain.

The first hybridizing region may be at a first opposite end of the first nucleic acid molecule from the first nonhybridizing region. For example, the first nucleic acid molecule can have the first hybridizing region at one end directly connected to the first nonhybridizing region. The first nucleic acid molecule may comprise one or more additional regions between the first hybridizing region and the first nonhybridizing region. For example, the first nucleic acid molecule can have the first hybridizing region connected to the first nonhybridizing region via a linker region. In this example, the linker region can be configured for an additional purpose (e.g., configured to bind to a detection moiety, etc.). The second hybridizing region may be at a second opposite end of the second nucleic acid molecule from the second nonhybridizing region. The second nucleic acid molecule may consist of the second hybridizing region and the second nonhybridizing region. The second nucleic acid molecule may comprise one or more additional regions between the second hybridizing region and the second nonhybridizing region.

In another operation 120, the method 100 may comprise coupling the first end of the first nucleic acid molecule and the second end of the second nucleic acid molecule to one another, thereby generating a nucleic acid product. The coupling may comprise coupling the first end and the second end to one another via a nucleic acid extension reaction. The nucleic acid extension reaction may be a nucleic acid extension reaction as described elsewhere herein. The coupling may comprise coupling the first end and the second end to one another via a nucleic acid ligation reaction. The ligation reaction may be a sticky end ligation (e.g., the first end and the second end can comprise unpaired nucleotides). The ligation reaction may be a blunt end ligation. The ligation reaction may comprise the use of an enzyme (e.g., a ligase, such as a DNA ligase). The ligation reaction may be made permanent by a creation of a phosphodiester bond between the first end and the second end. The ligation reaction may comprise the use of an additional oligonucleotide. For example, an additional oligonucleotide can be introduced that can bind to a portion of the first nucleic acid molecule as well as to the second nucleic acid molecule. In this example, the additional oligonucleotide can act as a bridge between the first nucleic acid molecule and the second nucleic acid molecule. The coupling may comprise coupling the first end and the second end to one another via a hybridization reaction. The hybridization reaction may be a hybridization reaction as described elsewhere herein. The coupling may comprise coupling the first end and the second end to one another via a nucleic acid extension reaction and a nucleic acid ligation reaction. For example, an oligonucleotide can be ligated between the first end and the second end, and a polymerase can be introduced to incorporate the ligated oligonucleotide, the first nucleic acid molecule, and the second nucleic acid molecule into a single nucleic acid product. The coupling may comprise coupling the first end and the second end to one another via a hybridization reaction and a nucleic acid ligation reaction as described elsewhere herein.

The first end of the first nucleic acid molecule and the second end of the second nucleic acid molecule may be adjacent (e.g., separated by a gap of zero nucleotides). For example, the first nucleic and molecule and the second nucleic acid molecule can be hybridized to the target nucleic acid molecule without any gap between them. In this example, the first end and the second end cannot have a gap between them as well. The first end of the first nucleic acid molecule and the second end of the second nucleic acid molecule may be separated by a gap of at least about 0, 1, 2, 3, 4, 5, 6, 7, 8, 9, 10, 15, 20, or more bases. The first end of the first nucleic acid molecule and the second end of the second nucleic acid molecule may be separated by a gap of at most about 20, 15, 10, 9, 8, 7, 6, 5, 4, 3, 2, 1, or fewer bases.

The method 100 may further comprise coupling the first opposite end and the second opposite end to one another. For example, coupling the first opposite end to the second opposite end as well as the first end to the second end can generate a circular nucleic acid product. In this example, the circular nucleic acid product can be configured to serve as a template for rolling circle amplification. The coupling the first opposite end and the second opposite end to one another may occur prior, during, or after operation 120. The coupling the first opposite end and the second opposite end to one another may comprise conducting a nucleic acid extension reaction as described elsewhere herein. For example, the first opposite end can be extended with the use of a polymerase to couple to the second opposite end. The coupling the first opposite end and the second opposite end to one another may comprise conducting a nucleic acid ligation reaction as described elsewhere herein. For example, adjacent first and second opposite ends can be coupled with the aid of a ligase. The coupling the first opposite end and the second opposite end to one another may comprise conducting a nucleic acid hybridization reaction as described elsewhere herein. For example, an oligonucleotide can be hybridized between the first and second opposite ends. The coupling the first opposite end and the second opposite end to one another may comprise conducting a nucleic acid extension reaction and a nucleic acid ligation reaction as described elsewhere herein. For example, the first opposite end can be extended to be adjacent to the second opposite end, and the two opposite ends can be ligated together. The coupling the first opposite end and the second opposite end to one another may comprise conducting a nucleic acid hybridization reaction and a nucleic acid ligation reaction as described elsewhere herein. For example, an oligonucleotide can be hybridized between the first and second opposite ends, and the first and second opposite ends can be ligated to the oligonucleotide, thus coupling the first and second opposite ends.

Prior to or during coupling the first opposite end and the second opposite end to one another, the opposite end of the first nucleic acid molecule and the opposite end of the second nucleic acid molecule may be adjacent (e.g., separated by a gap of zero nucleotides). For example, the first nucleic and molecule and the second nucleic acid molecule can be hybridized to the target nucleic acid molecule via the first and second opposite ends without any gap between them. The first opposite end of the first nucleic acid molecule and the second opposite end of the second nucleic acid molecule may be separated by a gap of at least about 0, 1, 2, 3, 4, 5, 6, 7, 8, 9, 10, 15, 20, or more bases. The first opposite end of the first nucleic acid molecule and the second opposite end of the second nucleic acid molecule may be separated by a gap of at most about 20, 15, 10, 9, 8, 7, 6, 5, 4, 3, 2, 1, or fewer bases.

The nucleic acid product or a derivative of the nucleic acid product may be used in a nucleic acid extension reaction to generate one or more nucleic acid extension products. For example, the nucleic acid product can be circular and thus can be used as a template for a rolling circle amplification to generate a concatemer nucleic acid extension product. In another example, the nucleic acid product can be non-circular and can be subjected to a polymerase to generate a clonal population of nucleic acid extension products. The nucleic acid product and/or derivative thereof may be a circular nucleic acid molecule. For example, both the first and second opposite ends as well as the first and second ends of the first and second nucleic acids can be linked to form a circular nucleic acid product. In another example, a nucleic acid derived from the nucleic acid product can be circularized. The nucleic acid extension reaction may comprise a rolling circle amplification reaction. The one or more nucleic acid extension products may comprise a concatemer. For example, a rolling circle amplification reaction can generate a concatemer as the product.

The method 100 may comprise detecting the one or more nucleic acid extension products and/or the one or more derivatives thereof. The detecting may be detecting as described elsewhere herein (e.g., optical detecting). For example, the detecting can be detecting via one or more fluorescent labels. The detecting may comprise sequencing the one or more nucleic acid extension products and/or the one or more derivatives thereof. The sequencing may be sequencing as described elsewhere herein. The sequencing may comprise a sequencing-by-synthesis reaction as described elsewhere herein. For example, blocked fluorescently labelled nucleotides can be introduced to the extension products in the presence of a polymerase, incorporated into a strand complementary to the extension products, detected via an optical detector, deblocked, and new blocked fluorescently labelled nucleotides can be introduced. In this example, the detection of the labelled nucleotides can be used to determine a sequence of the extension products. The sequencing may comprise a sequencing-by-hybridization reaction as described elsewhere herein. For example, an oligonucleotide comprising a detectable label can be introduced to a solution comprising the nucleic acid extension products and mismatch sensitive proteins (e.g., MutS), the oligonucleotide can hybridize to the nucleic acid extension product, the excess oligonucleotides can be washed away, and the hybridization of the oligonucleotide to the extension product can be detected via the detectable label. The sequencing may comprise a sequencing-by-ligation reaction as described elsewhere herein. The sequencing-by-ligation reaction may comprise the use of a ligase (e.g., a DNA ligase).

The method 100 may comprise hybridizing a sequence of a third nucleic acid molecule to at least a portion of the first nonhybridizing region or an additional sequence of the third nucleic acid molecule to at least a portion of the second nonhybridizing region. The hybridizing the sequence may occur prior to, during, or after operation 120. For example, a third nucleic acid molecule that is 80% complementary to the first nonhybridizing region can hybridize to the first non-hybridizing region. The method 100 may comprise hybridizing the sequence of the third nucleic acid molecule to the at least the portion of the first nonhybridizing region and the additional sequence of the third nucleic acid molecule to the at least the portion of the second nonhybridizing region. The hybridizing the sequence may occur prior to operation 120. The hybridizing the sequence may occur during operation 120. The hybridizing the sequence may occur after operation 120. For example, the third nucleic acid molecule that is 80% complementary to the first nonhybridizing region and 20% complementary to the second nonhybridizing region can hybridize to both the first and second nonhybridizing regions. The sequence of the third nucleic acid molecule may comprise at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The sequence of the third nucleic acid molecule may comprise at most about 50, 45, 40, 35, 30, 25, 20, 19, 18, 17, 16, 15, 14, 13, 12, 11, 10, 9, 8, 7, 6, 5, 4, 3, 2, or fewer nucleotides. The additional sequence of the third nucleic acid molecule may comprise at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The additional sequence of the third nucleic acid molecule may comprise at most about 50, 45, 40, 35, 30, 25, 20, 19, 18, 17, 16, 15, 14, 13, 12, 11, 10, 9, 8, 7, 6, 5, 4, 3, 2, or fewer nucleotides. In some embodiments, the additional sequence binding to the second nonhybridizing region is at least 1, 2, 3, 4, 5, 6, 7, 8, 9, 10, 11, 12, 13, 14, 15, 16, 17, 18, 19, 20, 25, 30, 35, 40, 45, 50, or fewer nucleotides than the sequence binding to the first nonhybridizing region. Alternatively, in some aspects, the additional sequence binding to the nonhybridizing region may also be about 5%, 10%, 15%, 20%, 25%, 30%, 35%, 40%, 45%, 50%, 55%, 60%, 65%, 70%, 75%, 80%, 85%, 90%, 95%, 100% shorter than sequence binding to the first nonhybridizing region. The additional sequence may have a lower melting temperature than that of the sequence. In some embodiments, the second nonhybridizing region binds to the additional sequence with a melting temperature of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 degrees Celsius less than the melting temperature between the first nonhybridizing region and the sequence. In some embodiments, the second nonhybridizing region binds to the additional sequence with a melting temperature that is between about 1 and 50, 1 and 45, 1 and 40, 1 and 35, 1 and 30, 1 and 25, 1 and 20, 1 and 15, 1 and 15, 1 and 10, 1 and 5, 5 and 50, 5 and 45, 5 and 40, 5 and 35, 5 and 30, 5 and 25, 5 and 20, 5 and 15, 5 and 10, 10 and 50, 10 and 45, 10 and 40, 10 and 35, 10 and 30, 10 and 25, 10 and 20, 10 and 15, 15 and 50, 15 and 45, 15 and 40, 15 and 35, 15 and 30, 15 and 25, 15 and 20, 20 and 50, 20 and 45, 20 and 40, 20 and 35, 20 and 30, 20 and 25, 25 and 50, 25 and 45, 25 and 40, 25 and 35, 25 and 30, 30 and 50, 30 and 45, 30 and 40, 30 and 35, 35 and 50, 35 and 45, 35 and 40, 40 and 50, 40 and 45, or 45 and 50 degrees Celsius less than the melting temperature the sequence binds to the first nonhybridizing region. The lower melting temperature may be due to the additional sequence being shorter than the sequence. For example, a sequence of 20 nucleotides can have a higher melting temperature than an additional sequence of 5 nucleotides. The lower melting temperature may be due to the additional sequence comprising fewer cytosine/guanine bases. In some embodiments, the portion of the additional sequence binding to the second nonhybridizing region may contain at least 1, 2, 3, 4, 5, 6, 7, 8, 9, 10, 11, 12, 13, 14, 15, 16, 17, 18, 19, 20, 25, 30, 35, 40, 45, 50 or fewer G/C nucleotides than the sequence binding to the first nonhybridizing region. In some embodiments, the portion of the additional sequence binding to the second nonhybridizing region may contain between 1 and 50, 1 and 50, 1 and 45, 1 and 40, 1 and 35, 1 and 30, 1 and 25, 1 and 20, 1 and 15, land 15, 1 and 10, 1 and 5, 5 and 50, 5 and 45, 5 and 40, 5 and 35, 5 and 30, 5 and 25, 5 and 20, 5 and 15, 5 and 10, 10 and 50, 10 and 45, 10 and 40, 10 and 35, 10 and 30, 10 and 25, 10 and 20, 10 and 15, 15 and 50, 15 and 45, 15 and 40, 15 and 35, 15 and 30, 15 and 25, 15 and 20, 20 and 50, 20 and 45, 20 and 40, 20 and 35, 20 and 30, 20 and 25, 25 and 50, 25 and 45, 25 and 40, 25 and 35, 25 and 30, 30 and 50, 30 and 45, 30 and 40, 30 and 35, 35 and 50, 35 and 45, 35 and 40, 40 and 50, 40 and 45, or 45 and 50 fewer G or C nucleotides than the sequence binding to the first nonhybridizing region. In alternative embodiments, the additional sequence binding to the second nonhybridizing region may have about 5%, 10%, 15%, 20%, 25%, 30%, 35%, 40%, 45%, 50%, 55%, 60%, 65%, 70%, 75%, 80%, 85%, 90%, 95% or 100% lower GC content than the sequence binding to the first nonhybridizing region. The difference in melting temperature may relate to a bound/unbound equilibrium of the third nucleic acid molecule. The additional sequence having a lower melting temperature than the sequence may result in more dynamic hybridization of the additional sequence to the second nonhybridizing region than the sequence to the first hybridizing region.

In some embodiments, the dynamic binding between the additional sequence and the second nonhybridizing sequence may allow for improved specificity of target detection, e.g., self-ligated probes giving rise to false positive signals are not detected.

The sequence may be hybridized to the first nonhybridizing region and the sequence may be used to conduct a nucleic acid extension reaction to generate a nucleic acid extension product. For example, the sequence can be a primer for a polymerase which can be used to generate the nucleic acid extension product. The sequence may be hybridized to the first nonhybridizing region prior to, during, or after operation 120. The nucleic acid extension reaction may comprise a rolling circle amplification reaction. For example, the third nucleic acid molecule can comprise a primer sequence for a rolling circle amplification polymerase and the third nucleic acid molecule can provide a binding site for the polymerase. The one or more nucleic acid extension products may comprise a concatemer. For example, the rolling circle amplification can generate a concatemer as its nucleic acid extension product.

The method 100 may comprise detecting the one or more nucleic acid extension products and/or one or more derivatives thereof. The detecting may be detecting as described elsewhere herein. The detecting may comprise sequencing the one or more nucleic acid extension products and/or the one or more derivatives thereof. The sequencing may be sequencing as described elsewhere herein. The sequencing may be sequencing-by-synthesis as described elsewhere herein, sequencing-by-hybridization as described elsewhere herein, sequencing-by-ligation as described elsewhere herein, or any combination thereof.

Operation 120 may comprise coupling the first end of and the second end to one another via a nucleic acid extension reaction. The nucleic acid extension reaction may comprise the use of a polymerase as described elsewhere herein. For example, a polymerase can extend the first end into the second end, thus coupling the first and second ends. Operation 120 may comprise coupling the first end and the second end to one another via a nucleic acid ligation reaction. The nucleic acid ligation reaction may comprise a nick repair reaction. In some cases, the first and second end can be adjacent to one another without a gap present, and a ligase (e.g., a DNA ligase) can connect the first end to the second end. In another example, the first and second end can be separated by a gap. In this example, the gap can be filled with an oligonucleotide, and a ligase can connect the first and second ends to the oligonucleotide, thus connecting the first and second ends. Operation 120 may comprise coupling the first end and the second end to one another via a hybridization reaction as described elsewhere herein. Operation 120 may comprise coupling the first end and the second end to one another via a nucleic acid extension reaction and a nucleic acid ligation reaction as described elsewhere herein. Operation 120 may comprise coupling the first end and the second end to one another via a hybridization reaction and a nucleic acid ligation reaction as described elsewhere herein.

Figure 2:
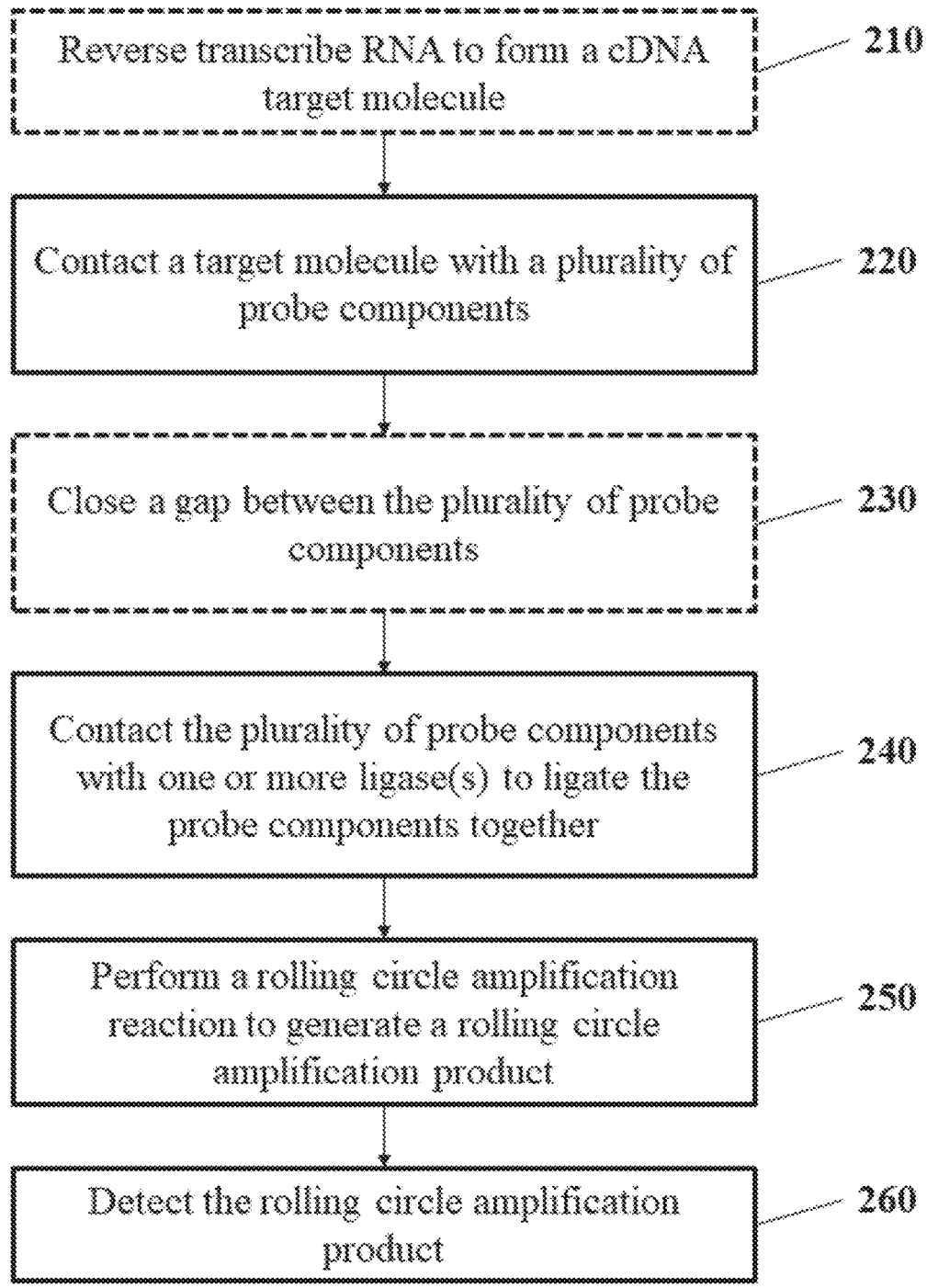
FIG. 2 is a flow chart of an exemplary process for nucleic acid processing. In some embodiments, the exemplary process comprises reverse transcribing RNA to form a cDNA target molecule. In some embodiments, a target molecule can be contacted with a plurality of probe components. In some embodiments, a gap between the plurality of probe components can be closed. In some embodiments, the plurality of probe components can be contacted with one or more ligase(s) to ligate the probe components together. In some embodiments, a rolling circle amplification reaction can be performed to generate a rolling circle amplification product. In some embodiments, the rolling circle amplification product can be detected.

FIG. 2 is a flow chart of an exemplary process 200 for nucleic acid processing. In an optional operation 210, the process 200 may comprise reverse transcribing RNA to form a complementary DNA (cDNA) target molecule. For example, if the sample comprises RNA, the sample can be subjected to reverse transcription in order to generate cDNA to the RNA. The RNA may be as described elsewhere herein. The RNA may be viral RNA. If the sample does not comprise RNA, operation 210 may be skipped.

In another operation 220, the process 200 may comprise contacting a target molecule with a plurality of probe components. The target molecule may be the cDNA target molecule. The target molecule may be a DNA molecule of a sample. For example, the target molecule can be a portion of a genome. The target molecule may be linked to a matrix as described elsewhere herein. For example, a cDNA molecule can be chemically linked to a 3D matrix. The plurality of probe components may be flowed into contact with the target molecule. For example, the target molecule can be immobilized on a matrix, and a solution comprising the plurality of probe components can be flowed into contact with the target molecule. The plurality of probe components may be at least about 2, 3, 4, 5, 6, 7, 8, 9, 10, or more probe components. The plurality of probe components may be at most about 10, 9, 8, 7, 6, 5, 4, 3, or fewer components. The plurality of components may be sized as to reduce a likelihood of self-circularization. For example, the plurality of components can be short enough that the strain of forming a circle can be high enough that the components are less likely to self-circularize. The plurality of components may be configured to have an increased diffusion rate to the target molecule. For example, a target molecule can be contained within a 3D matrix, which can significantly reduce the diffusion rate of a long probe to the target molecule. In this example, a plurality of shorter probe components can have an increased diffusion rate and thus reach the target molecule faster. The plurality of probe components may be configured as to separate functional regions of the probe. For example, a probe comprising two components can have a primer region on one component and a barcode region on the other component. Having separate functional regions can decrease a likelihood of a self-circularized probe component generating a false signal. For example, a self-circularized probe component with a barcode region but no primer region cannot bind a polymerase, thus decreasing the signal from the errantly self-circularized component. The plurality of probe components may be of a length to reduce or eliminate errors in the plurality of probe components during generation of the plurality of probe components. For example, since longer oligonucleotides can have increased error rates as opposed to shorter oligonucleotides, generating a plurality of probe components instead of as single long probe can reduce the number of errors present.

At least a portion of the plurality of probe components may be configured to bind to the target molecule. For example, two nucleic acid molecule probe components can each hybridize to different portions of the target molecule. Portions of the plurality of probe components may be configured to bind to other portions of the plurality of probe components. For example, a probe comprising 4 components can have two first components configured to hybridize to the target molecule, and two components configured to hybridize to the two first components. The contacting may comprise binding at least a portion of the plurality of probe components to the target molecule. The binding may be hybridization, antibody-antigen binding, or the like. The plurality of probe components may be contacted to the target molecule at a same time. For example, each of the plurality of probe components can be flowed into contact with the target molecule simultaneously. The plurality of probe components may be contacted to the target molecule at different times. For example, each of the plurality of probe components can be introduced sequentially to the target molecule. In this example, washing operations may be performed between each introduction to remove excess probe components.

In another operation 230, the process 200 may optionally comprise closing a gap between the plurality of probe components. The operation 230 may comprise closing a plurality of gaps between the plurality of probe components. For example, a gap between a first and a second probe component, as well as between the second and a third probe component can be closed. The gap closing may be making the plurality of probe components adjacent. The gap may be closed by hybridization, a nucleic acid extension reaction, or a combination thereof. The hybridization may be hybridization as described elsewhere herein (e.g., an oligonucleotide can be hybridized between the ends of the probe components). The nucleic acid extension reaction may be a nucleic acid extension reaction as described elsewhere herein (e.g., a polymerase can extend a first end of a first one of the probe components by nucleotide addition to be adjacent to a second end of a second of the probe components). If each of the plurality of probe components are already adjacent, operation 230 can be skipped.

In another operation 240, the process 200 may comprise contacting the plurality of probe components with one or more ligase(s) to ligate the probe components together. The one or more ligases may be ligases as described elsewhere herein. The contacting may be under conditions configured to activate the ligases for coupling the probe components, thus ligating the probe components together. The components of the plurality of probe components may be adjacent without a nucleotide gap, yet not coupled together. After operation 240, the plurality of probe components may be a single probe. For example, two probe components can be hybridized to a target cDNA, extended to become adjacent, and ligated to form a single circular probe. The circular probe may be configured to undergo amplification. The amplification may be a rolling circle amplification.

In another operation 250, the process 200 may comprise performing a rolling circle amplification reaction to generate a rolling circle amplification product. The rolling circle amplification may be a rolling circle amplification as described elsewhere herein. The rolling circle amplification may generate a concatemer comprising the regions of the plurality of probe components. For example, if a first probe component had a primer region and a second probe component had a barcode region, the concatemer can comprise repeated primer and component regions.

In another operation 260, the process 200 may comprise detecting the rolling circle amplification product. The rolling circle amplification product may be configured to generate an increased signal due to a presence of a plurality of binding sites for detection. The detecting may be detecting as described elsewhere herein. The detecting may be optical detecting (e.g., fluorescence intensity detecting, fluorescence lifetime detecting), electrical detecting, or the like, or any combination thereof.

Figure 3:
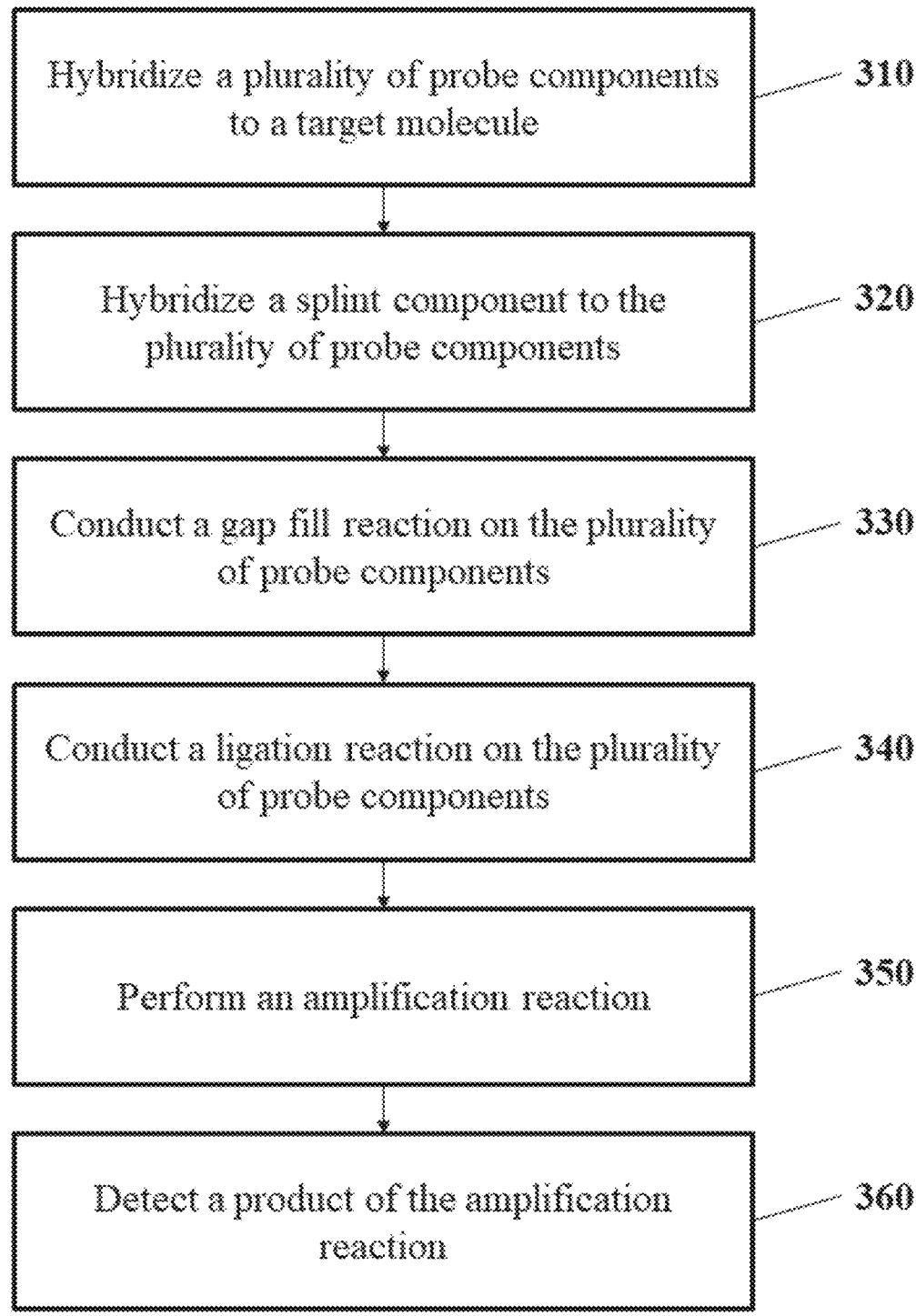
FIG. 3 is a flow chart of an exemplary process for assembling and using an exemplary multicomponent probe. In some embodiments, the exemplary process comprises hybridizing a plurality of probe components to a target molecule. In some embodiments, a splint component can hybridize to the plurality of probe components. In some embodiments, a gap between the probe components can be filled. In some embodiments, the plurality of probe components can be contacted with one or more ligase(s) to ligate the probe components together. In some embodiments, an amplification reaction can be performed. In some embodiments, the product of the amplification reaction can be detected.

FIG. 3 is a flow chart of an exemplary process 300 for assembling and using a multicomponent probe. In an operation 310, the process 300 may comprise hybridizing a plurality of probe components to a target molecule. The target molecule may be a target molecule as described elsewhere herein. The target molecule may be an analyte. The plurality of probe components may be a plurality of probe components as described elsewhere herein. The plurality of probe components may be directly hybridized to the target molecule. The plurality of probe components may be indirectly hybridized to the target molecule. For example, at least one component of the plurality of probe components can be hybridized to the target molecule via at least one other component of the plurality of probe components. The plurality of probe components may be configured not to hybridize to each other. For example, a probe comprising two components can be configured to not have overlapping regions that can hybridize. The plurality of probe components may be configured to hybridize to the target molecule on one end and leave the other end free.

In another operation 320, the process 300 may comprise hybridizing a splint component to the plurality of probe components. The splint component may hybridize to the ends of the plurality of probe components on the opposite side as the target molecule. For example, two probe components hybridized on a first side to the target molecule can have the splint component hybridize to the other side. The splint component may be an oligonucleotide. The splint component may be at least about 1, 2, 3, 4, 5, 6, 7, 8, 9, 10, 11, 12, 13, 14, 15, 16, 17, 18, 19, 20, 25, 30, 35, 40, 45, 50, or more nucleotides. The splint component may be at most about 50, 45, 40, 35, 30, 25, 20, 19, 18, 17, 16, 15, 14, 13, 12, 11, 10, 9, 8, 7, 6, 5, 4, 3, 2, or fewer nucleotides. The splint component may hybridize to two of the plurality of probe components. The splint component may hybridize equally to each of the plurality of probe components it is hybridized to. For example, a 24 base splint component can hybridize 12 bases to a first component and 12 bases to a second component. In another example, a 24 base splint component can hybridize 10 bases to a first component and 10 bases to a second component, leaving a gap of 4 bases between the probe components. The splint component may hybridize differently to each of the plurality of probe components. For example, a 30 base splint component can hybridize 25 bases to a first probe component and 5 bases to a second probe component. The difference in the number of splint bases hybridizing to the first and second nonhybridizing region may be 0, 1, 2, 3, 4, 5, 6, 7, 8, 9, 10 or more bases. In some embodiments, the difference in the number of splint bases hybridizing to the first and second nonhybridizing region may be between about 0 and 50, 0 and 45, 0 and 40, 0 and 35, 0 and 30, 0 and 25, 0 and 20, 0 and 15, 0 and 10, 0 and 5, 5 and 50, 5 and 45, 5 and 40, 5 and 35, 5 and 30, 5 and 25, 5 and 20, 5 and 15, 5 and 10, 10 and 50, 10 and 45, 10 and 40, 10 and 35, 10 and 30, 10 and 25, 10 and 20, 10 and 15, 15 and 50, 15 and 45, 15 and 40, 15 and 35, 15 and 30, 15 and 25, 15 and 20, 20 and 50, 20 and 45, 20 and 40, 20 and 35, 20 and 30, 20 and 25, 25 and 50, 25 and 45, 25 and 40, 25 and 35, 25 and 30, 30 and 50, 30 and 45, 30 and 40, 30 and 35, 35 and 50, 35 and 45, 35 and 40, 40 and 50, 40 and 45, or 45 and 50 bases. The splint component may be configured to have a different binding affinity to each of the plurality of probe components it is hybridized to (e.g., by adjusting the length of the splint, by changing the sequence of the splint, etc.). For example, the splint component can be configured to stably hybridize to a first probe component but dynamically hybridize to a second probe component. The splint component may be introduced to the plurality of probe components after the plurality of probe components have been hybridized to the target molecule.

In another operation 330, the process 300 may comprise conducting a gap fill reaction on the plurality of probe components. The gap fill reaction may be a nucleic acid extension reaction as described elsewhere herein. The gap fill reaction may be a hybridization reaction as described elsewhere herein. The gap fill reaction may use the splint component and/or the target molecule as a template. For example, a hybridization reaction to fill a gap between the probe components hybridized to the splint component can hybridize an oligonucleotide to the splint component between the probe components. In another example, a nucleic acid extension reaction to fill a gap between the probe components hybridized to the target molecule can use the target molecule as the substrate the polymerase reads from to fill in the bases for the extension reaction. After the gap fill reaction, the probe components may be adjacent. For example, the gap fill reaction can fill any gaps until all components are directly adjacent.

In another operation 340, the process 300 may comprise conducting a ligation reaction on the plurality of probe components. The ligation reaction may be a ligation reaction as described elsewhere herein. The ligation reaction may connect the plurality of probe components into a single probe. The probe may be a circular probe. The ligation reaction may be performed on any oligonucleotides added in a hybridization reaction. For example, if an oligonucleotide was hybridized between two probe components, the ligation reaction can link the probe components to the oligonucleotide.

In another operation 350, the process 300 may comprise performing an amplification reaction. The amplification reaction may be an amplification reaction as described elsewhere herein (e.g., a PCR amplification reaction). The amplification reaction may be a rolling circle amplification reaction as described elsewhere herein. For example, a circular probe can be subjected to a rolling circle amplification reaction. The amplification reaction may be performed on the target molecule. The amplification reaction may be performed on the probe. The amplification reaction may generate a plurality of copies of the probe. The amplification reaction may generate a product. The product may be a clonal population of nucleic acid molecules, a concatemer, or the like.

In another operation 360, the process 300 may comprise detecting a product of the amplification reaction. For example, the detecting can be of a concatemer generated by a rolling circle nucleic acid amplification reaction. The detecting may be detecting as described elsewhere herein. The detecting may be optical detecting. The optical detecting may be a detecting of fluorescent intensity, fluorescence peak wavelength position, fluorescence lifetime, absorption intensity, absorption peak wavelength position, or the like, or any combination thereof. For example, the optical detecting can be of the color (e.g., fluorescent wavelength position) of a dye. The optical detecting may be of an optical species associated with the product of the amplification reaction. The optical species may be an organic dye, a fluorophore, a nanoparticle, a protein, or the like, or any combination thereof. The detecting may be electrical detecting (e.g., detecting a change in electrical properties related to a sequencing event). The electrical detecting may comprise the use of a nanopore.

Figure 4:
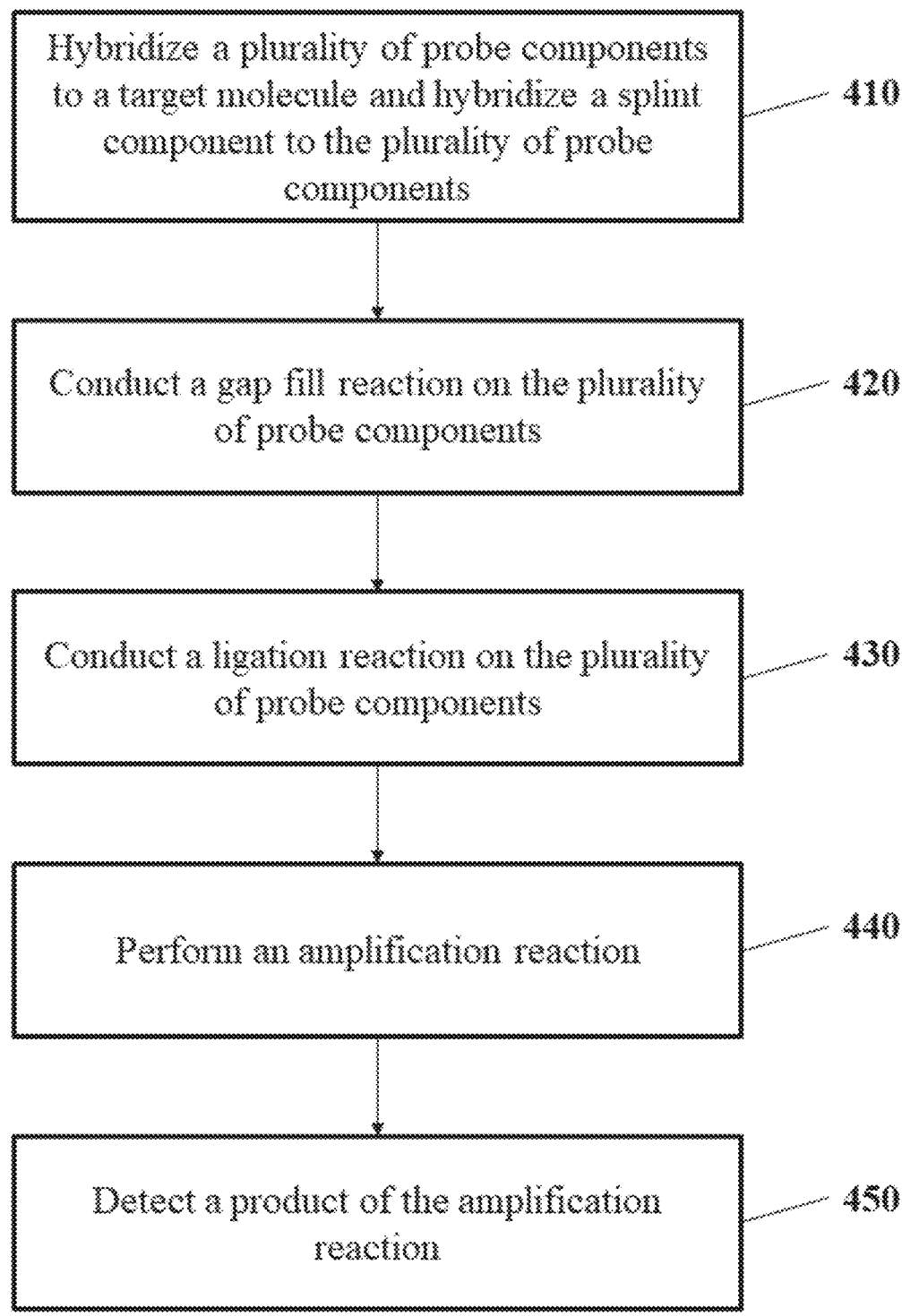
FIG. 4 is a flow chart of an exemplary process for assembling and using an exemplary multicomponent probe. In some embodiments, the exemplary process comprises hybridizing a plurality of probe components to a target molecule and hybridizing a splint component to the probe components. In some embodiments, a gap between the probe components can be closed. In some embodiments, an amplification reaction can be performed. In some embodiments, the product of the amplification can be detected.

FIG. 4 is a flow chart of an exemplary process 400 for assembling and using a multicomponent probe. In an operation 410, the process 400 may comprise hybridizing a plurality of probe components to a target molecule and hybridizing a splint component to the plurality of probe components. The plurality of probe components may be in a same solution as the splint component. The plurality of probe components may hybridize to the target molecule before the splint component hybridizes to the plurality of probe components. The splint component may hybridize to at least one probe component before the plurality of probe components hybridize to the target molecule. For example, the splint component can hybridize to a to a probe component in solution, the plurality of probe components can hybridize to the target molecule, and then the splint component can hybridize to another probe component. The splint component may be configured to hybridize stably to a first probe component in solution but not hybridize stably to a second probe component. The splint component may be configured to not stably hybridize to both of the probe components in solution to reduce a chance of self-circularization and false signal.

In another operation 420, the process 400 may comprise conducting a gap fill reaction on the plurality of probe components. The gap fill reaction may be a nucleic acid extension reaction as described elsewhere herein. The gap fill reaction may be a hybridization reaction as described elsewhere herein. The gap fill reaction may use the splint component and/or the target molecule as a template. For example, a hybridization reaction to fill a gap between the probe components hybridized to the splint component can hybridize an oligonucleotide to the splint component between the probe components. In another example, a nucleic acid extension reaction to fill a gap between the probe components hybridized to the target molecule can use the target molecule as the substrate the polymerase reads from to fill in the bases for the extension reaction. After the gap fill reaction, the probe components may be adjacent. For example, the gap fill reaction can fill any gaps until all components are directly adjacent.

In another operation 430, the process 400 may comprise conducting a ligation reaction on the plurality of probe components. The ligation reaction may be a ligation reaction as described elsewhere herein. The ligation reaction may connect the plurality of probe components into a single probe. The probe may be a circular probe. The ligation reaction may be performed on any oligonucleotides added in a hybridization reaction. For example, if an oligonucleotide was hybridized between two probe components, the ligation reaction can link the probe components to the oligonucleotide.

In another operation 440, the process 400 may comprise performing an amplification reaction. The amplification reaction may be an amplification reaction as described elsewhere herein (e.g., a PCR amplification reaction). The amplification reaction may be a rolling circle amplification reaction as described elsewhere herein. For example, a circular probe can be subjected to a rolling circle amplification reaction. The amplification reaction may be performed on the target molecule. The amplification reaction may be performed on the probe. The amplification reaction may generate a plurality of copies of the probe. The amplification reaction may generate a product. The product may be a clonal population of nucleic acid molecules, a concatemer, or the like.

In another operation 450, the process 400 may comprise detecting a product of the amplification reaction. For example, the detecting can be of a concatemer generated by a rolling circle nucleic acid amplification reaction. The detecting may be detecting as described elsewhere herein. The detecting may be optical detecting. The optical detecting may be a detecting of fluorescent intensity, fluorescent wavelength position, fluorescence lifetime, absorption intensity, absorption wavelength, or the like, or any combination thereof. For example, the optical detecting can be of the color (e.g., fluorescent wavelength position) of a dye. The optical detecting may be of an optical species associated with the product of the amplification reaction. The optical species may be an organic dye, a fluorophore, a nanoparticle, a protein, or the like, or any combination thereof. The detecting may be electrical detecting (e.g., detecting a change in electrical properties related to a sequencing event). The electrical detecting may comprise the use of a nanopore.

Figure 5:
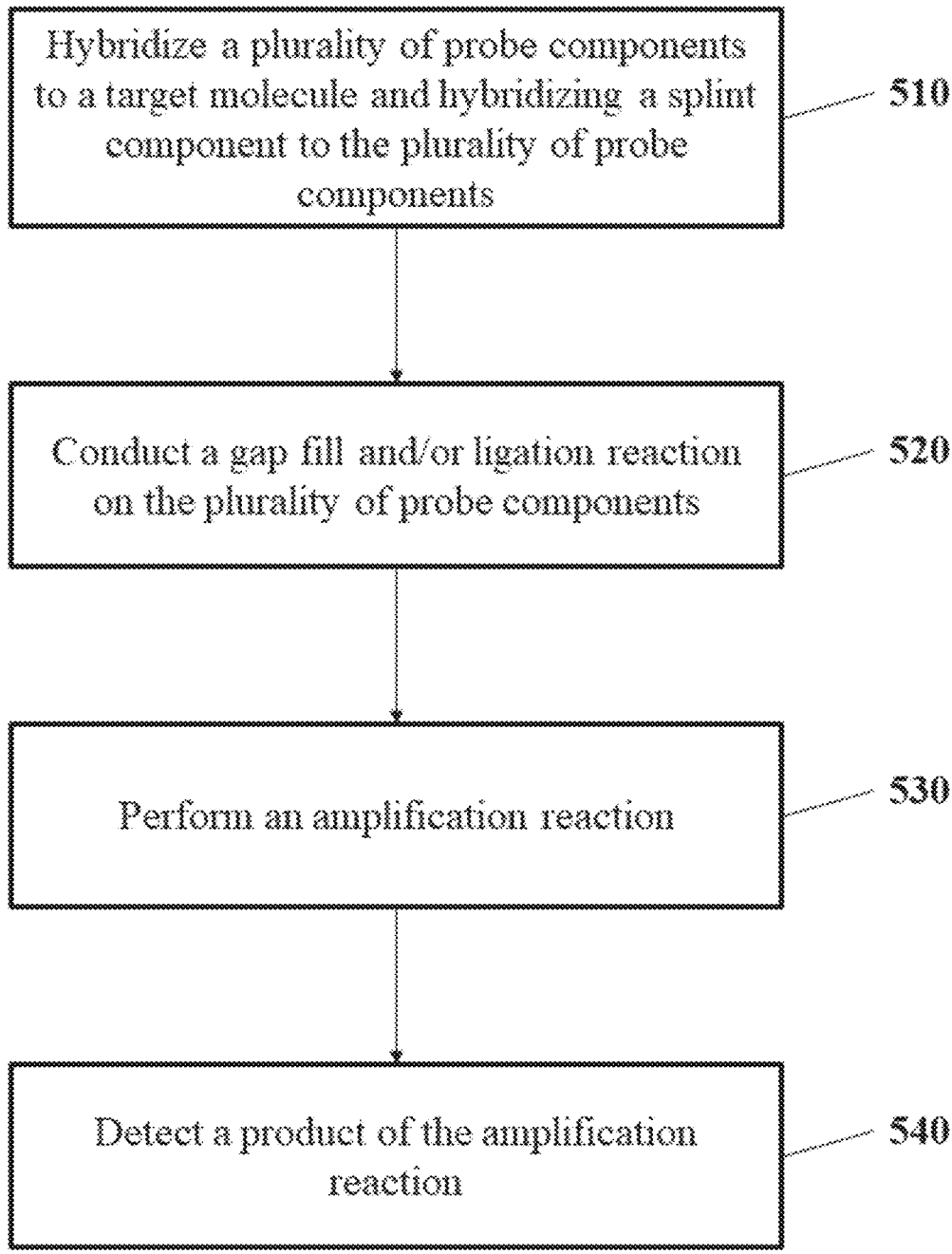
FIG. 5 is a flow chart of an exemplary process for assembling and using an exemplary multicomponent probe. In some embodiments, the exemplary process comprises hybridizing a plurality of probe components to a target molecule and hybridizing a splint component to the probe components. In some embodiments, a gap between the probes can be filled. In some embodiments, the probe components can be ligated together. In some embodiments, an amplification reaction can be performed. In some embodiments, the product of the amplification can be detected.

FIG. 5 is a flow chart of an exemplary process 500 for assembling and using a multicomponent probe. In an operation 510, the process 500 may comprise hybridizing a plurality of probe components to a target molecule and hybridizing a splint component to the plurality of probe components. The plurality of probe components may be in a same solution as the splint component. The plurality of probe components may hybridize to the target molecule before the splint component hybridizes to the plurality of probe components. The splint component may hybridize to at least one probe component before the plurality of probe components hybridize to the target molecule. For example, the splint component can hybridize to a to a probe component in solution, the plurality of probe components can hybridize to the target molecule, and then the splint component can hybridize to another probe component. The splint component may be configured to hybridize stably to a first probe component in solution but not hybridize stably to a second probe component. The splint component may be configured to not stably hybridize to both of the probe components in solution to reduce a chance of self-circularization and false signal.

In another operation 520, the process 500 may comprise conducting a gap fill and/or ligation reaction on the plurality of probe components. Operation 520 may not comprise a gap fill reaction if the ends of the probe components are already adjacent. For example, if the probe components are adjacent on the target molecule and adjacent on the splint component, operation 520 can comprise a ligation reaction without a gap fill reaction. The gap fill reaction may be a gap fill reaction as described elsewhere herein. The ligation reaction may be a ligation reaction as described elsewhere herein. After operation 520, the plurality of probe components may be a single probe.

In another operation 530, the process 500 may comprise performing an amplification reaction. The amplification reaction may be an amplification reaction as described elsewhere herein (e.g., a PCR amplification reaction). The amplification reaction may be a rolling circle amplification reaction as described elsewhere herein. For example, a circular probe can be subjected to a rolling circle amplification reaction. The amplification reaction may be performed on the target molecule. The amplification reaction may be performed on the probe. The amplification reaction may generate a plurality of copies of the probe. The amplification reaction may generate a product. The product may be a clonal population of nucleic acid molecules, a concatemer, or the like.

In another operation 540, the process 500 may comprise detecting a product of the amplification reaction. For example, the detecting can be of a concatemer generated by a rolling circle nucleic acid amplification reaction. The detecting may be detecting as described elsewhere herein. The detecting may be optical detecting. The optical detecting may be a detecting of fluorescent intensity, fluorescent wavelength position, fluorescence lifetime, absorption intensity, absorption wavelength, or the like, or any combination thereof. For example, the optical detecting can be of the color (e.g., fluorescent wavelength position) of a dye. The optical detecting may be of an optical species associated with the product of the amplification reaction. The optical species may be an organic dye, a fluorophore, a nanoparticle, a protein, or the like, or any combination thereof. The detecting may be electrical detecting (e.g., detecting a change in electrical properties related to a sequencing event). The electrical detecting may comprise the use of a nanopore.

FIG. 6 is a flow chart of an exemplary process 600 for assembling and using a multicomponent probe. In an operation 610, the process 600 may comprise (i) hybridizing a plurality of probe components to a target molecule, (ii) hybridizing a splint component to the plurality of probe components, and (iii) performing a gap fill and/or ligation reaction on the plurality of probe components. Each of elements (i)-(ii) may be performed in any order. Element (iii) may follow elements (i) and (ii). All of elements (i)-(iii) may be performed at substantially the same time. For example, a solution comprising the plurality of probe components, the ligase/gap fill enzymes, and the splint component can be flowed into contact with the target molecule. In this example, each of the elements can occur at substantially the same time because all components of the elements are present at the same time. The gap fill reaction may be a gap fill reaction as described elsewhere herein. The ligation reaction may be a ligation reaction as described elsewhere herein. At the end of operation 610, the plurality of probe components may form a single probe.

In another operation 620, the process 600 may comprise conducting an amplification reaction. The amplification reaction may be an amplification reaction as described elsewhere herein (e.g., a PCR amplification reaction). The amplification reaction may be a rolling circle amplification reaction as described elsewhere herein. For example, a circular probe can be subjected to a rolling circle amplification reaction. The amplification reaction may be performed on the target molecule. The amplification reaction may be performed on the probe. The amplification reaction may generate a plurality of copies of the probe. The amplification reaction may generate a product. The product may be a clonal population of nucleic acid molecules, a concatemer, or the like.

In another operation 630, the process 600 may comprise detecting a product of the amplification reaction. For example, the detecting can be of a concatemer generated by a rolling circle nucleic acid amplification reaction. The detecting may be detecting as described elsewhere herein. The detecting may be optical detecting. The optical detecting may be a detecting of fluorescent intensity, fluorescent wavelength position, fluorescence lifetime, absorption intensity, absorption wavelength, or the like, or any combination thereof. For example, the optical detecting can be of the color (e.g., fluorescent wavelength position) of a dye. The optical detecting may be of an optical species associated with the product of the amplification reaction. The optical species may be an organic dye, a fluorophore, a nanoparticle, a protein, or the like, or any combination thereof. The detecting may be electrical detecting (e.g., detecting a change in electrical properties related to a sequencing event). The electrical detecting may comprise the use of a nanopore.

III. Three-Dimensional (3D) Matrix

The present disclosure provides a three-dimensional (3D) matrix. The 3D matrix may comprise a plurality of nucleic acids. The 3D matrix may comprise a plurality of nucleic acids covalently or non-covalently attached thereto. The 3D matrix can be a gel matrix. The 3D matrix can be a hydrogel matrix. The 3D matrix can preserve an absolute or relative 3D position of the plurality of nucleic acid molecules. Methods for embedding a sample in a matrix have been described in, e.g., US2016/0024555, US2019/0276881, US2020/0071751, WO2020/0076976, WO2020/0076979, and WO2020/0096687, which are incorporated herein by reference in their entirety.

In some cases, a matrix-forming material may be used to form the 3D matrix. The matrix-forming material may be polymerizable monomers or polymers, or cross-linkable polymers. The matrix-forming material may be polyacrylamide, acrylamide monomers, cellulose, alginate, polyamide, agarose, dextran, or polyethylene glycol. The matrix-forming materials can form a matrix by polymerization and/or crosslinking of the matrix-forming materials using methods specific for the matrix-forming materials and methods, reagents, and conditions. The matrix-forming material may form a polymeric matrix. The matrix-forming material may form a polyelectrolyte gel. The matrix-forming material may form a hydrogel gel matrix.

The matrix-forming material may form a 3D matrix including the plurality of nucleic acids while maintaining the spatial relationship of the nucleic acids. In this aspect, the plurality of nucleic acids can be immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise cross-linking with the matrix-forming material. The plurality of nucleic acids may also be immobilized within the matrix by covalent attachment or through ligand-protein interaction to the matrix.

The matrix can be porous thereby allowing the introduction of reagents into the matrix at the site of a nucleic acid for amplification of the nucleic acid. A porous matrix may be made according to various methods. For example, a polyacrylamide gel matrix can be co-polymerized with acrydite-modified streptavidin monomers and biotinylated DNA molecules, using a suitable acrylamide:bis-acrylamide ratio to control the cross-linking density. Additional control over the molecular sieve size and density can be achieved by adding additional cross-linkers such as functionalized polyethylene glycols.

The 3D matrix may be sufficiently optically transparent or may have optical properties suitable for standard sequencing chemistries and deep three-dimensional imaging for high throughput information readout. Examples of the sequencing chemistries that utilize fluorescence imaging include ABI SoLiD (Life Technologies), in which a sequencing primer on a template is ligated to a library of fluorescently labeled octamers with a cleavable terminator. After ligation, the template can then be imaged using four color channels (FITC, Cy3, Texas Red and Cy5). The terminator can then be cleaved off leaving a free-end to engage in the next ligation-extension cycle. After all dinucleotide combinations have been determined, the images can be mapped to the color code space to determine the specific base calls per template. The workflow can be achieved using an automated fluidics and imaging device (e.g., SoLiD 5500 W Genome Analyzer, ABI Life Technologies). Another example of sequencing platform uses sequencing by synthesis, in which a pool of single nucleotide with a cleavable terminator can be incorporated using DNA polymerase. After imaging, the terminator can be cleaved, and the cycle can be repeated. The fluorescence images can then be analyzed to call bases for each DNA amplicons within the flow cell (HiSeq, Illumina).

IV. Immobilization to 3D Matrix

In various aspects of the present disclosure, a tethering molecule can be used to attach an analyte or derivative thereof (e.g., an amplicon derived from an analyte) to the three-dimensional (3D) matrix. The tethering molecule can be a nucleic acid molecule having a sequence complementary to a sequence of the target nucleic acid molecule. In some cases, the tethering molecule can have a free 3' end that can be extended in a polymerization reaction. For example, the tethering molecule can be a primer. The primer can be a reverse transcription (RT) primer targeting ribonucleic acid molecules. The primer can be a poly-dT primer. In some cases, the primer can be a padlock RT primer. The tethering molecule may be a primer. The tethering primer may be one of the components. For example, the tethering primer can be the splint. In some cases where the analyte is a polypeptide molecule (e.g., a protein), the polypeptide molecule may be bound by a binding agent linked to a nucleic acid sequence, which can then be detected by the methods and systems provided herein. For example, the binding agent can be a nucleic acid barcode conjugated antibody or antibody fragment. The tethering molecule can have a sequence complementary to the nucleic acid barcode of the antibody or fragment thereof. In some cases, the binding agent comprising a nucleic acid barcode can itself function as a tethering molecule, which can be used to attach the binding agent to the 3D matrix directly. In such cases, the nucleic acid barcode may comprise a tethering moiety for attaching to the 3D matrix.

The tethering molecule can comprise a tethering moiety for attaching the tethering molecule to the 3D matrix. The 3D matrix can comprise an attachment moiety. The tethering moiety can bind to the attachment moiety such that the tethering molecule can be attached to the 3D matrix. The tethering moiety and the attachment moiety can be functional moieties that can react with each other. The tethering moiety and the attachment moiety can be click functional moieties that react with each other via click chemistry, such as CUAAC click chemistry. For example, the tethering moiety can be an alkyne, and the attachment moiety can be an azide, or vice versa. Examples of click functional moieties include, but are not limited to, an amine, a thiol, an azide, an alkyne, a nitrone, an alkene, a tetrazine, a tetrazole and an acrydite. As used herein, the term "reactive group" or "functional moiety" generally refers to any moiety on a first reactant that is capable of reacting chemically with another functional moiety or reactive group on a second reactant to form a covalent or ionic linkage. For example, a reactive group of the monomer or polymer of the matrix-forming material can react chemically with a functional moiety (or another reactive group) on the substrate of interest or the target to form a covalent or ionic linkage. The substrate of interest or the target may then be immobilized to the matrix via the linkage formed by the reactive group and the functional moiety. Examples of suitable reactive groups or functional moieties include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like. The tethering moiety and the attachment moiety can be a binding pair, for example, protein-protein binding pair. The tethering moiety and the attachment moiety can form a non-covalent interaction, for example, an ionic interaction, a Van der Waals force, a hydrophobic interaction, and a hydrogen bonding. The tethering moiety can be a biotin, and the attachment moiety can be a streptavidin, or vice versa.

In some cases, other nucleic acids (e.g., RNA molecule, cDNA molecule, primer, or probe) described herein may comprise a functional moiety. The nucleic acids can be linked to the 3D matrix by the functional moiety. The functional moiety can be reacted with a reactive group on the 3D matrix through conjugation chemistry. In some cases, the functional moiety can be attached to target of interest through conjugation chemistry. In some cases, the functional moiety can be directly attached to a reactive group on the native nucleic acid molecule. In some cases, the functional moiety can be indirectly linked to a target through an intermediate chemical or group. The conjugation strategies described herein are not limited to nucleic acid targets and can be used for protein or small molecule targets as well. A nucleotide analog comprising a functional moiety may be incorporated into a growing chain of the nucleic acid (e.g., cDNA molecule, probe, or primer) during nucleic acid synthesis or an extension reaction.

The cDNA molecule may be functionalized during the reverse transcription reaction, such as by adding nucleotide triphosphate analogs comprising functional moieties for immobilization. The circular probe and/or the RCA product may also be functionalized by adding nucleotide triphosphate analogs comprising functional moieties. Such nucleotide triphosphate analogs include, but are not limited to, amino-allyl dUTP, 5-TCO-PEG4-dUTP, C8-Alkyne-dUTP, 5-Azidomethyl-dUTP, 5-Vinyl-dUTP, 5-Ethynyl dUTP, and other nucleotide triphosphate analogs comprising a functional moiety for cDNA immobilization by cross-linking or forming a chemical bond between the cDNA and the in situ matrix, cellular or synthetic. Furthermore, the in-situ matrix, cellular or synthetic, may contain or be made to contain chemical moieties (e.g., reactive groups) that can react with the functional moieties in the cDNA through functionalization reactions. For example, amino-allyl dUTP may be cross-linked to endogenous free amine groups present in proteins and other biomolecules present within the endogenous or exogenous cellular matrix, or present in a modified synthetic hydrogel matrix, such as an amine-functionalized polyacrylamide hydrogel formed by copolymerization of polyacrylamide and N-(3-aminopropyl)-methacrylamide; likewise nucleoside analogs containing azide functional moieties may be cross-linked to a synthetic hydrogel matrix comprising alkyne functional moieties, such as that formed by copolymerization of acrylamide and propargyl acrylamide.

The target nucleic acid molecule (e.g., cDNA molecule) may be functionalized with moieties for immobilization subsequent to reverse transcription. Mechanisms for post-synthesis cDNA functionalization may include a variety of biochemical and chemical methods. These include, but are not limited to, use of a ligation reaction to conjugate an oligonucleotide bearing a functional moiety for immobilization to the cDNA molecule, use of a DNA polymerization reaction to add templated or un-templated bases to the cDNA, as in the process of A-tailing by Taq polymerize, or by using the reactions mediated by DNA end-repair mechanisms. Alternatively, a chemical method of DNA chemical functionalization may be used to conjugate functional moieties for immobilization. For example, Label-IT Amine and Label-X are bifunctional reagents that can react with nucleic acids via a nitrogen mustard alkylation mechanism for the purpose of conjugating free amine or acryloyl groups to the nucleic acid, which can be used for the purpose of immobilization to the matrix. Other chemistries, including but not limited to, DNA alkylation and oxymercuration, can provide mechanisms for functionalizing DNA. The circular probe and/or the RCA product may also be functionalized with moieties for immobilization disclosed herein.

The present disclosure provides a method of modifying a nucleic acid in situ to comprise a functional moiety. In some cases, the functional moiety may comprise a polymerizable group. In some cases, the functional moiety may comprise a free radical polymerizable group. In some cases, the functional moiety may comprise an amine, a thiol, an azide, an alkyne, a nitrone, an alkene, a tetrazine, a tetrazole, an acrydite, or other click reactive group. In some cases, the functional moiety can be subsequently linked to a 3D matrix in situ. The functional moiety may further be used to preserve the absolute or relative spatial relationships among two or more molecules within a sample.

V. Supports

A matrix may be used in conjunction with a support (e.g., a solid or semi-solid support). For example, the matrix can be polymerized in such a way that one surface of the matrix is attached to a support (e.g., a glass surface, a flow cell, a glass slide, a well), while the other surface of the matrix is exposed or sandwiched between two solid supports. According to one aspect, the matrix can be contained within a container. In some cases, the biological sample may be fixed or immobilized on a support. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose The support of the present disclosure may be fashioned into a variety of shapes. In certain embodiments, the support is substantially planar. Examples of support include plates such as slides, multiwell plates, flow cells, coverslips, microchips, and the like, containers such as microfuge tubes, test tubes and the like, tubing, sheets, pads, films, and the like. Additionally, the support may be, for example, biological, non-biological, organic, inorganic, or a combination thereof.

As used herein, the term "solid surface" is intended to mean the surface of a solid or semi-solid support and includes any material that can serve as a solid or semi-solid foundation for attachment of a biological sample or other molecules such as polynucleotides, amplicons, DNA balls, other nucleic acids, and/or other polymers, including bio-polymers. Example types of materials comprising solid surfaces include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those above, and multiwell plates. Example types of plastics include, but are not limited to, acrylics, polystyrene, copolymers of styrene and other materials, polypropylene, polyethylene, polybutylene, polyurethanes, and Teflon™. Example types of silica-based materials include, but are not limited to, silicon and various forms of modified silicon (e.g., silicon/oxygen compounds).

Solid surfaces can also be varied in their shape depending on the application in a method described herein. For example, a solid surface useful in the present disclosure can be planar, or contain regions which are concave or convex.

In some embodiments, the solid surface can be coated or functionalized with one or more substances to facilitate attachment of the sample to the substrate. Suitable substances that can be used to coat or functionalize the substrate include, but are not limited to, lectins, poly-lysine, antibodies, and polysaccharides.

VI. Biological Samples

A biological sample may be provided in the methods, systems, and compositions described herein. The biological sample can comprise the analyte to be processed and/or detected using the methods described herein.

In some aspects, a biological sample may be fixed in the presence of the matrix-forming materials such as, for example, hydrogel subunits. The term "fixing," as used herein with reference to the biological sample, generally refers to exposing the biological sample, e.g., cells or tissues, to a fixation agent such that the cellular components become crosslinked to one another. The terms "hydrogel" or "hydrogel network," as used herein, generally refer to a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels may also possess a degree of flexibility very similar to natural tissue, due to their significant water content. The terms "hydrogel subunits" or "hydrogel precursors," as used herein, generally refer to hydrophilic monomers, prepolymers, or polymers that can be crosslinked, or "polymerized", to form a 3D hydrogel network. Without being bound by any scientific theory, fixation of the biological sample in the presence of hydrogel subunits may crosslink the components of the biological sample to the hydrogel subunits, thereby securing molecular components in place, preserving the tissue architecture and cell morphology.

In some cases, the biological sample (e.g., cell or tissue) may be permeabilized or otherwise made accessible to an environment external to the biological sample. In some cases, the biological sample may be fixed and permeabilized first, and then a matrix-forming material can then be added into the biological sample.

Any suitable biological sample that comprises a nucleic acid may be obtained from a subject. Any suitable biological sample that comprises a nucleic acid may be used in the methods and systems described herein. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. A biological sample may be a cell-free sample. Such cell-free sample may include DNA and/or RNA.

Tissues can be obtained from a subject using any variety of techniques including, but not limited to, biopsy, surgery, and laser capture microscopy (LCM), and generally includes cells and/or other biological material from the subject. A biological sample may be a cell-free sample. Such cell-free sample may include DNA and/or RNA. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 μm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 μm. Thicker sections can also be used if desired or convenient, e.g., at least 70, 80, 90, or 100 μm or more. Typically, the thickness of a tissue section is between 1-100 μm, 1-50 μm, 1-30 μm, 1-25 μm, 1-20 μm, 1-15 μm, 1-10 μm, 2-8 μm, 3-7 μm, or 4-6 μm, but as mentioned above, sections with thicknesses larger or smaller than these ranges can also be analyzed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to obtain three-dimensional information about the biological sample.

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

Any convenient fixation agent, or "fixative," may be used to fix the biological sample in the absence or in the presence of hydrogel subunits, for example, formaldehyde, paraformaldehyde, glutaraldehyde, acetone, ethanol, methanol, etc. The fixative may be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/ 0.1M phosphate buffer; 2% paraformaldehyde/0.2% picric acid/0.1M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative may depend on the sensitivity of the molecules of interest in the specimen to denaturation by the fixative and may be readily determined using histochemical or immunohistochemical techniques. In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

The fixative/hydrogel composition may comprise any hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly (hydroxyethyl methacrylate), collagen, hyaluronic acid, chitosan, dextran, agarose, gelatin, alginate, protein polymers, methylcellulose and the like. Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability. Materials such as block copolymers of PEG, degradable PEO, poly(lactic acid) (PLA), and other similar materials can be used to add specific properties to the hydrogel. Crosslinkers (e.g. bis-acrylamide, diazirine, etc.) and initiators (e.g. azobisisobutyronitrile (AIBN), riboflavin, L-arginine, etc.) may be included to promote covalent bonding between interacting macromolecules in later polymerization operations.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 µm to about 2 mm.

The biological sample (e.g., a cell or tissue) may be permeabilized after being fixed. Permeabilization may be performed to facilitate access to cellular cytoplasm or intracellular molecules, components, or structures of a cell. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable. Permeabilization may allow an agent (such as a phospho-selective antibody, a nucleic acid conjugated antibody, a nucleic acid probe, a primer, etc.) to enter into a cell and reach a concentration within the cell that is greater than that which normally penetrates into the cell in the absence of such permeabilizing treatment. In some embodiments, cells may be stored following permeabilization. In some cases, the cells may be contacted with one or more agents to allow penetration of the one or more agents after permeabilization without any storage operation and then analyzed. In some embodiments, cells may be permeabilized in the presence of at least about 60%, 70%, 80%, 90% or more methanol (or ethanol) and incubated on ice for a period of time. The period of time for incubation can be at least about 10, 15, 20, 25, 30, 35, 40, 50, 60 or more minutes.

In some embodiments, permeabilization of the cells may be performed by any suitable method. Selection of an appropriate permeabilizing agent and optimization of the incubation conditions and time may be performed. Suitable methods include, but are not limited to, exposure to a detergent (such as CHAPS, cholic acid, deoxycholic acid, digitonin, n-dodecyl-beta-D-maltoside, lauryl sulfate, glycodeoxycholic acid, n-lauroylsarcosine, saponin, triton X-100) or to an organic alcohol (such as methanol or ethanol). Other permeabilizing methods can comprise the use of certain peptides or toxins that render membranes permeable. Permeabilization may also be performed by addition of an organic alcohol to the cells.

Permeabilization can also be achieved, for example, by way of illustration and not limitation, through the use of surfactants, detergents, phospholipids, phospholipid binding proteins, enzymes, viral membrane fusion proteins and the like; through the use of osmotically active agents; by using chemical crosslinking agents; by physicochemical methods including electroporation and the like; or by other permeabilizing methodologies. For instance, cells may be permeabilized using any of a variety of techniques, such as exposure to one or more detergents (e.g., digitonin, Triton X-100™, NP-40™, octyl glucoside and the like) at concentrations below those used to lyse cells and solubilize membranes (e.g., below the critical micelle concentration). Certain transfection reagents, such as dioleoyl-3-trimethylammonium propane (DOTAP), may also be used. Adenosine triphosphate (ATP) can also be used to permeabilize intact cells. Low concentrations of chemicals used as fixatives (e.g., formaldehyde) may also be used to permeabilize intact cells.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

The biological sample within the 3D matrix may be cleared of proteins and/or lipids that are not targets of interest. For example, the biological sample can be cleared of proteins (also called "deproteination") by enzymatic proteolysis. The clearing operation may be performed before or after covalent immobilization of any target molecules or derivatives thereof.

In some cases, the clearing operation is performed after covalent immobilization of target nucleic acid molecules (e.g., RNA or DNA), primers (e.g., RT primers), derivatives of target molecules (e.g., cDNA or amplicons), probes (e.g., padlock probes, probes described elsewhere herein) to a synthetic 3D matrix. Performing the clearing operation after immobilization can enable any subsequent nucleic acid hybridization reactions to be performed under conditions where the sample has been substantially deproteinated, as by enzymatic proteolysis (e.g., "protein clearing"). This method can have the benefit of removing ribosomes and other RNA- or nucleic-acid-target-binding proteins from the target molecule (while maintaining spatial location), where the protein component may impede or inhibit primer binding, reverse transcription, or probe ligation and amplification, thereby improving the sensitivity and quantitativity of the assay by reducing bias in probe capture events due to protein occupation of or protein crowding/proximity to the target nucleic acid.

The clearing operation can comprise removing non-targets from the 3D matrix. The clearing operation can comprise degrading the non-targets. The clearing operation can comprise exposing the sample to an enzyme (e.g., a protease) able to degrade a protein. The clearing operation can comprise exposing the sample to a detergent.

Proteins may be cleared from the sample using enzymes, denaturants, chelating agents, chemical agents, and the like, or any combination thereof, which may break down the proteins into smaller components and/or amino acids. These smaller components may be easier to remove physically, and/or may be sufficiently small or inert such that they do not significantly affect the background. Similarly, lipids may be cleared from the sample using surfactants or the like. In some cases, one or more of these agents are used, e.g., simultaneously or sequentially. Non-limiting examples of suitable enzymes include proteinases such as proteinase K, proteases or peptidases, or digestive enzymes such as trypsin, pepsin, or chymotrypsin. Non-limiting examples of suitable denaturants include guanidine HCl, acetone, acetic acid, urea, and lithium perchlorate. Non-limiting examples of chemical agents able to denature proteins include solvents such as phenol, chloroform, guanidinium isocyananate, urea, formamide, etc. Non-limiting examples of surfactants include Triton X-100 (polyethylene glycol p-(1,1,3,3-tetramethylbutyl)-phenyl ether), SDS (sodium dodecyl sulfate), Igepal CA-630, and poloxamers. Non-limiting examples of chelating agents include ethylenediaminetetraacetic acid (EDTA), citrate, and polyaspartic acid. In some embodiments, compounds such as these may be applied to the sample to clear proteins, lipids, and/or other components. For instance, a buffer solution (e.g., containing Tris or tris(hydroxymethyl)aminomethane) may be applied to the sample, then removed.

In some cases, nucleic acids that are not target of interest may also be cleared. These non-target nucleic acids may not be captured and/or immobilized to the 3D matrix, and therefore can be removed with an enzyme to degrade nucleic acid molecules. Non-limiting examples of DNA enzymes that may be used to remove DNA include DNase I, dsDNase, a variety of restriction enzymes, etc. Non-limiting examples of techniques to clear RNA include RNA enzymes such as RNase A, RNase T, or RNase H, or chemical agents, e.g., via alkaline hydrolysis (for example, by increasing the pH to greater than 10). Non-limiting examples of systems to remove sugars or extracellular matrices include enzymes such as chitinase, heparinases, or other glycosylases. Non-limiting examples of systems to remove lipids include enzymes such as lipidases, chemical agents such as alcohols (e.g., methanol or ethanol), or detergents such as Triton X-100 or sodium dodecyl sulfate. In this way, the background of the sample may be removed, which may facilitate analysis of the nucleic acid probes or other targets, e.g., using fluorescence microscopy, or other techniques as described herein.

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine. The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, a biological sample embedded in a matrix (e.g., a hydrogel) can be isometrically expanded. Isometric expansion methods that can be used include hydration, a preparative step in expansion microscopy, as described in Chen et al., Science 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE or "AcX") (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

VII. Analytes

Provided herein are methods and compositions for analyte (e.g., nucleic acid) analysis. The analyte may be a target of interest in a biological sample. In some cases, the analyte may include any biological substance, structure, moiety, or compound analyzed. In some cases the analyte may be a nucleic acid molecule. In some cases, the analyte may be a nucleic acid barcode. In some cases, the nucleic acid barcode can comprise a tethering moiety, which can link the nucleic acid barcode to a 3D matrix. In such cases, the binding agent may itself function as a tethering molecule. In some cases, the nucleic acid barcode can be linked to a 3D matrix through a tethering molecule comprising a nucleic acid sequence complementary to the nucleic acid barcode and a tethering moiety for attaching to the 3D matrix. The nucleic acid analyte can be a ribonucleic acid (RNA) or a deoxyribonucleic acid (DNA). The nucleic acid analyte may be naturally occurring nucleic acids or non-naturally occurring nucleic acids, such as nucleic acids that have been made using synthetic methods.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The nucleic acid targets, whether naturally occurring or synthetic, can be present within a three-dimensional (3D) matrix and covalently attached to the 3D matrix such that the relative position of each nucleic acid is fixed (e.g., immobilized) within the 3D matrix. In this manner, a 3D matrix of covalently bound nucleic acids of any sequence can be provided. Each nucleic acid may have its own three-dimensional coordinates within the matrix material and each nucleic acid may represent information. In this manner, a large amount of information can be stored in a 3D matrix. Individual information-encoding nucleic acid target, such as DNA or RNA can be amplified and sequenced in situ (e.g., within the matrix), thereby enabling a large amount of information to be stored and read in a suitable 3D matrix. Naturally occurring nucleic acid targets can include endogenous DNAs and RNAs. Synthetic nucleic acid targets can include primers, barcodes, amplification products and probes. The synthetic nucleic acid targets may be derived from the endogenous nucleic acid molecules or include sequence information of the endogenous nucleic acid molecules. The synthetic nucleic acid targets can be used to capture endogenous nucleic acid targets to the 3D matrix and can be subsequently sequenced or detected to identity the sequence information and/or positional (or spatial) information of the endogenous nucleic acid molecules. For example, a synthetic nucleic acid target can be a primer having a poly-deoxythymine (dT) sequence, which can hybridize to an endogenous mRNA molecule. The primer may be immobilized to the 3D matrix and may be extended to include sequence information (e.g., a sequence) of the mRNA molecule. The extended primer can then be captured by probes, including probes described elsewhere herein, and amplified in situ for detection. In another example, a synthetic nucleic acid target can be a barcode conjugated on an antibody. The barcode may be captured by probes, including probes described elsewhere herein, and amplified in situ for detection. The nucleic acid target can be an endogenous nucleic acid in a biological sample. Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

The nucleic acid target can also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

The nucleic acid target may be a synthetic nucleic acid linked to a binding agent. The binding agent may bind to any biological molecules to be detected in a biological sample. For example, to detect a protein, the binding agent may be an antibody or a portion thereof having a nucleic acid sequence linked thereto. For another example, to detect a protein, the binding agent may be an aptamer.

The nucleic acid target may be amplified to produce amplification products or amplicons within the 3D matrix. The nucleic acid target may be amplified using nucleic acid amplification, such as, for example, polymerase chain reaction (PCR). The nucleic acid target may be bound to a probe and the probe may be subsequently amplified to produce amplification products or amplicons. In some cases, the nucleic acid target is an RNA target, and the RNA target may be reverse transcribed to generate a cDNA. The cDNA may then be subjected to amplification or may be contacted with a probe, including a multi-component probe described elsewhere herein. The probe can hybridize with the cDNA. In some cases, the nucleic acid target is a DNA target, and the DNA target can be subjected to amplification or can be contacted with a probe, including a multi-component probe described elsewhere herein. For example, the DNA target can be amplified directly by an amplification primer. In another example, a padlock probe or circular probe generated by joining the multicomponent probes described herein (e.g., the first and second probes) may be contacted with the DNA target and hybridize to the DNA target. The padlock probe can then be circularized and amplified. The amplification products or amplicons can be attached to the matrix, for example, by copolymerization or cross-linking. This can result in a structurally stable and chemically stable 3D matrix of nucleic acids. The 3D matrix of nucleic acids may allow for prolonged information storage and read-out cycles. The nucleic acid/amplicon matrix may allow for high throughput sequencing of a wide-ranging array of samples in three dimensions.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, BMC Genomics, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, Biotechniques, 53(6) 373-80, (2012), the entire contents of which are incorporated herein by reference).

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent, for example, the circularization of a circularizable probe or probe set upon hybridization to a target sequence. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5′-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adapter sequence, a unique molecular identifier (UMI) sequence, a sequencer specific flow cell attachment sequence (such as an P5, P7, or partial P5 or P7 sequence), a primer or primer binding sequence, a sequencing primer or primer binding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

A biological sample may comprise one or a plurality of analytes of interest. Methods for performing multiplexed assays to analyze two or more different analytes in a single biological sample are provided.

VIII. Probe Hybridization and Ligation

In some embodiments, a nucleic acid product disclosed herein (e.g., a circular probe) can be assembled from multiple components, e.g., during and/or after contacting a target nucleic acid or a sample with the multiple components. In some embodiments, the nucleic acid product disclosed herein is assembled in situ in a sample. In some embodiments, the multiple components can be contacted with a target nucleic acid or a sample in any suitable order and any suitable combination. For instance, a first component and a second component can be contacted with a target nucleic acid, to allow binding between the components and/or binding between the first and/or second components with the target nucleic acid. Optionally a reaction involving either or both components and/or the target nucleic acid, between the components, and/or between either one or both components and the target nucleic acid can be performed, such as hybridization, ligation, primer extension and/or amplification, chemical or enzymatic cleavage, click chemistry, or any combination thereof. In some embodiments, a third component can be added prior to, during, or after the reaction. In some embodiments, a third component can be added prior to, during, or after contacting the sample with the first and/or second components. In some embodiments, the first, second, and third components can be contacted with the sample in any suitable combination, sequentially or simultaneously. In some embodiments, the nucleic acid probe can be assembled in situ in a stepwise manner, each step with the addition of one or more components, or in a dynamic process where all components are assembled together. One or more removing steps, e.g., by washing the sample such as under stringent conditions, may be performed at any point during the assembling process to remove or destabilize undesired intermediates and/or components at that point and increase the chance of accurate probe assembly and specific target binding of the assembled probe.

The multiple components can be coupled (e.g., ligated) to form the nucleic acid product (e.g., the circular probe). Multiple ligation points in a hybridization complex disclosed herein can be catalyzed by the same ligase or by different ligases, and can occur simultaneously (e.g., in the same reaction volume) or in any suitable order.

In some embodiments, provided herein is a multicomponent probe set capable of DNA-templated ligation, such as from a cDNA molecule. In some embodiments, provided herein is a multicomponent probe set (e.g., first and second nucleic acid molecules) capable of RNA-templated ligation. In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a SplintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity. In some embodiments, the ends of the first and second probes can be ligated using a ligase selected from the group consisting of a *Chlorella* virus DNA ligase (PBCV DNA ligase), a T4 RNA ligase, a T4 DNA ligase, and a single-stranded DNA (ssDNA) ligase, such as a PBCV-1 DNA ligase or variant or derivative thereof, a T4 RNA ligase 2 (T4 Rnl2) or variant or derivative thereof, or a CircLigase™ or variant or derivative thereof (e.g., CircLigase™ I or CircLigase™ II).

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower Tm around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

IX. Amplification

Any type of nucleic acid amplification reaction may be used to perform an amplification reaction in the methods or systems described herein and generate an amplification product. Moreover, amplification of a nucleic acid may be linear, exponential, or a combination thereof. Non-limiting examples of nucleic acid amplification methods include transcription (e.g., in vitro transcription), reverse transcription, primer extension, polymerase chain reaction, ligase chain reaction, helicase-dependent amplification, asymmetric amplification, rolling circle amplification, and multiple displacement amplification (MDA). In some cases, the amplified product may be DNA. In cases where a target RNA is amplified, DNA can be obtained by reverse transcription of the RNA and subsequent amplification of the DNA can be used to generate an amplified DNA product. In some cases, a target RNA is reverse transcribed by a reverse transcriptase to generate a cDNA. In some cases, a target DNA is transcribed by an RNA polymerase to generate an RNA. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touch-down PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

The amplification of nucleic acid sequences may be performed within the matrix. Methods of amplifying nucleic acids may include rolling circle amplification in situ. The rolling circle amplification may generate an amplicon. The amplicon may be linked to the matrix. The linkage to the matrix may be a linkage to the matrix as described elsewhere herein. For example, the amplicon can be linked to the matrix by the incorporation of a functional nucleotide. In another example, the amplicon can be linked to the matrix by a tethering moiety on the primer that is extended to form the amplicon. In certain aspects, methods of amplifying nucleic acids may include the use of PCR, such as anchor PCR, RACE PCR, or a ligation chain reaction (LCR). Alternative amplification methods include but are not limited to self-sustained sequence replication, transcriptional amplification system, Q-Beta Replicase, recursive PCR, or any other nucleic acid amplification method.

The nucleic acids within the 3D matrix may be contacted with reagents under suitable reaction conditions sufficient to amplify the nucleic acids. The matrix may be porous to allow migration of reagents into the matrix to contact the nucleic acids. In certain aspects, nucleic acids may be amplified by selectively hybridizing an amplification primer to an amplification site at the 3' end of a nucleic acid sequence. Amplification primers can be 6 to 100, and even up to 1,000, nucleotides in length. Amplification primers can be from 10 to 40 nucleotides in length, although oligonucleotides of different length are of use. In some cases, the amplification primer can be at least about 5, 6, 7, 8, 9, 10, 11, 12, 13, 14, 15, 16, 17, 18, 19, 20, 21, 22, 23, 24, 25, or more nucleotides in length. In some cases, the amplification primer can be at least about 20, 30, 40, 50, 60, 70, 80, 90, 100, 200, 300, 400, 500, or more nucleotides in length. Amplification primers may hybridize to a nucleic acid probe that hybridizes to a DNA molecule such that the amplification primers can be used to amplify a sequence of the nucleic acid probe. Amplification primers may be present in solution to be added to the matrix or they may be added during formation of the matrix to be present therein sufficiently adjacent to nucleic acids to allow for hybridization and amplification.

A polymerase can be used in an amplification reaction. Any suitable polymerase may be used, including a DNA polymerase. A DNA polymerase generally refers to an enzyme that is capable of incorporating nucleotides to a strand of DNA in a template bound fashion. Non-limiting examples of polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products, and derivatives thereof. Other enzymes can also be used for an amplification reaction, including but not limited to, an RNA polymerase (e.g., T7 RNA polymerase, SP6 RNA polymerase, T3 RNA polymerase, etc.) and a reverse transcriptase (e.g., Avian myeloblastosis virus (AMV) reverse transcriptase, a wild type human immunodeficiency virus-1 (HIV-1) reverse transcriptase, or a Moloney Murine Leukemia Virus (M-MLV) reverse transcriptase).

In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the modified nucleotide comprises an azide-dNTP such as azide-dUTP. In some embodiments, the modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

X. Detection

The present disclosure provides methods and systems for sample processing for use in nucleic acid detection. A sequence of the nucleic acid target may be identified. Various methods can be used for nucleic acid detection, including hybridization and sequencing. Nucleic acid detection can comprise imaging the biological sample or the 3D matrix described herein.

Reporter agents may be linked with nucleic acids, including amplified products, by covalent or non-covalent interactions. Non-limiting examples of non-covalent interactions include ionic interactions, Van der Waals forces, hydrophobic interactions, hydrogen bonding, and combinations thereof. Reporter agents may bind to initial reactants and changes in reporter agent levels may be used to detect amplified product. Reporter agents may be detectable (or non-detectable) as a nucleic acid amplification progresses. Reporter agents may be optically detectable. An optically-active dye (e.g., a fluorescent dye) may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2 (and 3)-5-(Acetylmercapto)-succinyl]amino}fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, a reporter agent may be a sequence-specific oligonucleotide probe that is optically active when hybridized with a nucleic acid target or derivative thereof (e.g., an amplified product). A probe may be linked to any of the optically-active reporter agents (e.g., dyes) described herein and may also include a quencher capable of blocking the optical activity of an associated dye. Non-limiting examples of probes that may be used as reporter agents include TaqMan probes, TaqMan Tamara probes, TaqMan MGB probes, or Lion probes.

In some aspects, the method for determining the nucleic acid sequence of a target nucleic acid molecule includes sequencing. In some aspects, sequencing by synthesis (SBS), sequencing by ligation (SBL), or sequencing by hybridization (SBH) can be used for determining the nucleic acid sequence of a target nucleic acid molecule. As disclosed herein, various amplification methods can be employed to generate larger quantities, particularly of limited nucleic acid samples, prior to sequencing. For example, the amplification methods can produce a targeted library of amplicons.

For sequencing by hybridization, labeled oligonucleotides or oligonucleotides that can be labeled may be hybridized to the target nucleic acid molecule and detected to determine the presence of a sequence of the target nucleic acid complementary to the labeled oligonucleotides or oligonucleotides that can be labeled. The detection of the labeled oligonucleotides or the oligonucleotides that can be labeled may be a detection of the label. The detection may be a detection as described elsewhere herein (e.g., an optical detection of a fluorescent label). Examples of sequencing by hybridization are provided in U.S. Pat. No. 10,227,639 and U.S. publication number 2019/0218608, both of which are herein incorporated by reference in their entirety for all purposes.

For sequencing by ligation, labeled nucleic acids or nucleic acids that can be labeled may be hybridized, identified, and successively ligated to determine the sequence of a target nucleic acid molecule. In some cases, such labeled nucleic acids or nucleic acids that can be labeled can be interrogated with a nucleic acid probe. Such a nucleic acid probe may comprise a label (e.g., an optical label, such as a fluorescent label). Examples of nucleic acids that can be used in sequencing-by ligation methods are provided in U.S. Pat. No. 10,501,791, which is herein incorporated by reference in its entirety for all purposes. For sequencing by synthesis (SBS), labeled nucleotides can be used to determine the sequence of a target nucleic acid molecule. A target nucleic acid molecule can be hybridized with a primer and incubated in the presence of a polymerase and a labeled nucleotide containing a blocking group. The primer can be extended such that the labeled nucleotide is incorporated. The presence of the blocking group may permit the incorporation of a single nucleotide. The presence of the label can permit identification of the incorporated nucleotide. As used herein, a label can be any optically active dye described herein. Either single bases can be added or, alternatively, all four bases can be added simultaneously, particularly when each base is associated with a distinguishable label. After identifying the incorporated nucleotide by its corresponding label, both the label and the blocking group can be removed, thereby allowing a subsequent round of incorporation and identification. Thus, cleavable linkers can link the label to the base. Examples of cleavable linker include, but are not limited to, peptide linkers. Additionally, a removable blocking group may be used so that multiple rounds of identification can be performed, thereby permitting identification of at least a portion of the target nucleic acid sequence. The compositions and methods disclosed herein are useful for such an SBS approach. In addition, the compositions and methods can be useful for sequencing from a solid support (e.g., an array or a sample within a 3D matrix as described herein), where multiple sequences can be "read" simultaneously from multiple positions on the solid support since each nucleotide at each position can be identified based on its identifiable label. Example methods are described in US 2009/0088327; US 2010/0028885; and US 2009/0325172, each of which is incorporated herein by reference.

In some embodiments, a method disclosed herein comprises a barcode sequencing method in which barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 2019/0055594 and U.S. Pat. Pub. 2021/0164039, which are hereby incorporated by reference in their entirety.

In some aspects, the provided methods involve analyzing, e.g., detecting or determining, one or more sequences present in the polynucleotides and/or in a product or derivative thereof, such as in a circular probe generated by joining the multicomponent probes described herein (e.g., the first and second probes). In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

In any of the embodiments herein, barcodes can be analyzed (e.g., detected or sequenced) using any suitable methods or techniques, including those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS), targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the preceding embodiments, the methods provided herein can include analyzing the barcodes by sequential hybridization and detection with a plurality of labelled probes (e.g., detection oligos).

XI. Computer Systems

Figure 8:
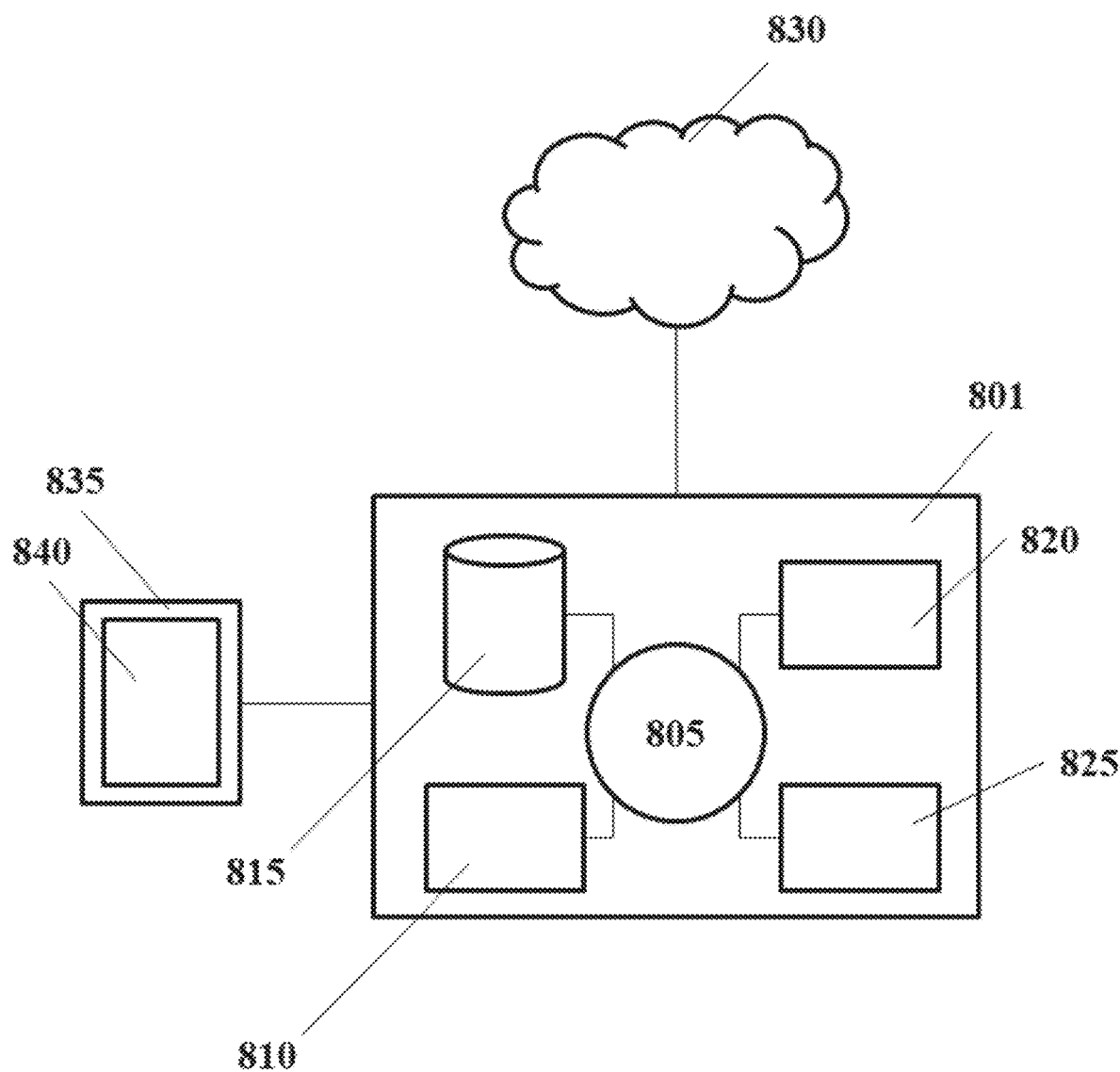
FIG. 8 shows an example computer system that is programmed or otherwise configured to implement methods provided herein.

The present disclosure provides computer systems that are programmed to implement methods of the disclosure. FIG. 8 shows a computer system 801 that is programmed or otherwise configured to implement methods of analyzing a target nucleic acid molecule. The computer system 801 can regulate various aspects of the present disclosure, such as, for example, controlling the operations of analyzing a target nucleic acid molecule. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries, and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a cloud computing system, a server system). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine-readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, an interface to start and/or monitor the progress of a nucleic acid identification. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, determine optimal conditions for implementing the methods and using the compositions of the present disclosure.

XII. Compositions, Kits, and Methods of Use

Also provided are compositions and kits, for example, comprising one or more nucleic acid molecules of the nucleic acid molecules describes herein and reagents for performing the methods provided herein, for example, reagents required for one or more steps including hybridization, ligation, amplification, detection, sequencing, sample preparation, embedding and/or anchoring as described herein.

In some embodiments, provided herein is a composition for nucleic acid analysis, comprising: a first nucleic acid molecule comprising (i) a first hybridizing region having a first sequence complementary to a first target sequence of a target nucleic acid molecule and (ii) a first nonhybridizing region at a first end of said first nucleic acid molecule; and a second nucleic acid molecule comprising (i) a second hybridizing region having a second sequence complementary to a second target sequence of said target nucleic acid molecule and (ii) a second nonhybridizing region at a second end of said second nucleic acid molecule, wherein said first nucleic acid molecule and said second molecule are configured such that, upon hybridization of said first sequence to said first target sequence and said second sequence to said second target sequence: (1) said first nonhybridizing region and said second nonhybridizing region do not hybridize with said target nucleic acid molecule; and (2) said first end and said second end undergo coupling to one another.

In any of the embodiments disclosed herein, said first nucleic acid molecule and said second molecule can be configured such that, upon hybridization of said first sequence to said first target sequence and said second sequence to said second target sequence, said first end and said second end undergo coupling to one another via a nucleic acid extension reaction.

In any of the embodiments disclosed herein, said first nucleic acid molecule and said second molecule can be configured such that, upon hybridization of said first sequence to said first target sequence and said second sequence to said second target sequence, said first end and said second end undergo coupling to one another via a nucleic acid ligation reaction.

In any of the embodiments disclosed herein, said first nucleic acid molecule and said second molecule can be configured such that, upon hybridization of said first sequence to said first target sequence and said second sequence to said second target sequence, said first end and said second end undergo coupling to one another via a hybridization reaction.

In any of the embodiments disclosed herein, said first nucleic acid molecule and said second molecule can be configured such that, upon hybridization of said first sequence to said first target sequence and said second sequence to said second target sequence, said first end and said second end undergo coupling to one another via a nucleic acid extension reaction and a nucleic acid ligation reaction.

In any of the embodiments disclosed herein, said first nucleic acid molecule and said second molecule can be configured such that, upon hybridization of said first sequence to said first target sequence and said second sequence to said second target sequence, said first end and said second end undergo coupling to one another via a hybridization reaction and a nucleic acid ligation reaction.

In any of the embodiments disclosed herein, said first nucleic acid molecule and said second molecule can be configured such that, upon hybridization of said first sequence to said first target sequence and said second sequence to said second target sequence, said first end of said first nucleic acid molecule and said second end of said second nucleic acid molecule are adjacent. In any of the embodiments disclosed herein, said first nucleic acid molecule and said second molecule can be configured such that, upon hybridization of said first sequence to said first target sequence and said second sequence to said second target sequence, said first end of said first nucleic acid molecule and said second end of said second nucleic acid molecule are separated by a gap of no more than 100 nucleotides.

In any of the embodiments disclosed herein, said first hybridizing region can be at a first opposite end of said first nucleic acid molecule from said first nonhybridizing region. In any of the embodiments disclosed herein, said second hybridizing region is at a second opposite end of said second nucleic acid molecule from said second nonhybridizing region.

In any of the embodiments disclosed herein, said first nucleic acid molecule and said second molecule can be configured such that, upon hybridization of said first sequence to said first target sequence and said second sequence to said second target sequence, said first opposite end and said second opposite end undergo coupling to one another via a nucleic acid extension reaction.

In any of the embodiments disclosed herein, said first nucleic acid molecule and said second molecule can be configured such that, upon hybridization of said first sequence to said first target sequence and said second sequence to said second target sequence, said first opposite end and said second opposite end undergo coupling to one another via a nucleic acid ligation reaction.

In any of the embodiments disclosed herein, said first nucleic acid molecule and said second molecule can be configured such that, upon hybridization of said first sequence to said first target sequence and said second sequence to said second target sequence, said first opposite end and said second opposite end undergo coupling to one another via a hybridization reaction.

In any of the embodiments disclosed herein, said first nucleic acid molecule and said second molecule can be configured such that, upon hybridization of said first sequence to said first target sequence and said second sequence to said second target sequence, said first opposite end and said second opposite end undergo coupling to one another via a nucleic acid extension reaction and a nucleic acid ligation reaction.

In any of the embodiments disclosed herein, said first nucleic acid molecule and said second molecule can be configured such that, upon hybridization of said first sequence to said first target sequence and said second sequence to said second target sequence, said first opposite end and said second opposite end undergo coupling to one another via a hybridization reaction and a nucleic acid ligation reaction.

In any of the embodiments disclosed herein, said first nucleic acid molecule and said second molecule can be configured such that, upon hybridization of said first sequence to said first target sequence and said second sequence to said second target sequence, said opposite end of said first nucleic acid molecule and said opposite end of said second nucleic acid molecule are adjacent. In any of the embodiments disclosed herein, said first nucleic acid molecule and said second molecule can be configured such that, upon hybridization of said first sequence to said first target sequence and said second sequence to said second target sequence, said opposite end of said first nucleic acid molecule and said opposite end of said second nucleic acid molecule are separated by a gap of no more than 100 nucleotides.

In any of the embodiments disclosed herein, the composition can further comprise a third nucleic acid molecule. In any of the embodiments disclosed herein, a sequence of said third nucleic acid molecule can be complementary to at least a portion of said first nonhybridizing region. In any of the embodiments disclosed herein, the sequence can comprise at least 10 nucleotides. In any of the embodiments disclosed herein, the sequence can be hybridized with said at least said portion of said first nonhybridizing region. In any of the embodiments disclosed herein, an additional sequence of said third nucleic acid molecule can be complementary to at least a portion of said second nonhybridizing region. In any of the embodiments disclosed herein, the additional sequence can comprise at most 10 nucleotides. In any of the embodiments disclosed herein, the additional sequence can be configured to have a lower melting temperature than that of said sequence. In any of the embodiments disclosed herein, the additional sequence can be hybridized with said at least said portion of said second nonhybridizing region. In any of the embodiments disclosed herein, the sequence can be hybridized with said at least said portion of said first nonhybridizing region and said additional sequence can be hybridized with said at least said portion of said second nonhybridizing region.

In any of the embodiments disclosed herein, the composition can further comprise said target nucleic acid molecule. In any of the embodiments disclosed herein, the first sequence can be hybridized with said first target sequence. In any of the embodiments disclosed herein, the second sequence can be hybridized with said second target sequence.

In any of the embodiments disclosed herein, a third end of said third nucleic acid molecule can comprise an exonuclease-resistant moiety. In any of the embodiments disclosed herein, said exonuclease-resistant moiety can be a phosphorothioate linkage.

In any of the embodiments disclosed herein, said third nucleic acid molecule can comprise a primer sequence configured for nucleic acid amplification. In any of the embodiments disclosed herein, said primer sequence can be configured for rolling circle amplification, e.g., the third nucleic acid molecule or a portion thereof can be used to prime a rolling circle amplification, e.g., using a circular molecule comprising the first and second nucleic acid molecules connected to each other as a template.

In any of the embodiments disclosed herein, the composition can further comprise said target nucleic acid molecule immobilized in a biological sample and/or in a matrix embedding the biological sample or molecules thereof. In any of the embodiments disclosed herein, said target nucleic acid molecule can be complementary deoxyribonucleic acid (cDNA) derived from reverse transcribed ribonucleic acid (RNA). In any of the embodiments disclosed herein, said target nucleic acid molecule can be a messenger ribonucleic acid (mRNA) molecule. In any of the embodiments disclosed herein, said target nucleic acid molecule can be a genomic nucleic acid molecule.

In any of the embodiments disclosed herein, the composition can further comprise a three-dimensional (3D) matrix. In any of the embodiments disclosed herein, the target nucleic acid molecule can be immobilized to said 3D matrix.

In any of the embodiments disclosed herein, said first nonhybridizing region may not have a sequence complementarity to said first target sequence. In any of the embodiments disclosed herein, said second nonhybridizing region may not have a sequence complementarity to said second target sequence.

In any of the embodiments disclosed herein, said first nucleic acid molecule may comprise a sequencing primer binding site. In any of the embodiments disclosed herein, said second nucleic acid molecule may comprise a barcode domain.

In some embodiments, provided herein is a hybridization complex comprising a first nucleic acid molecule and a second nucleic acid molecule, wherein: the first nucleic acid comprises a first hybridizing region, and a first nonhybridizing region, the second nucleic acid comprises a second hybridizing region and a second non hybridizing region, and the first and second nucleic acid are capable of hybridizing to a target nucleic acid, wherein the first and second hybridizing regions hybridize to the target region and the first and second nonhybridizing regions do not hybridize to the target nucleic acid. In some embodiments, the first and second nucleic acids are DNA molecules and the target nucleic acid is a DNA (e.g., cDNA or genomic DNA) molecule. In some embodiments, the first and second nucleic acids are DNA molecules and the target nucleic acid is an RNA (e.g., mRNA) molecule. In some embodiments, the hybridization complex further comprises the target nucleic acid hybridized to the first and second nucleic acids. In some embodiments, the first nucleic acid molecule is any as described herein. In some embodiments, the second nucleic acid molecule is any as described herein.

In some embodiments, provided herein is a hybridization complex comprising a first nucleic acid, a second nucleic acid, and a splint, wherein: the first nucleic acid comprises a first hybridizing region, and a first nonhybrizing region, the second nucleic acid comprises a second hybridizing region and a second nonhybridizing region, and the first and second nucleic acid are capable of hybridizing to a target nucleic acid, wherein the first and second hybridizing regions hybridize to the target region and first and second nonhybridizing regions hybridize to the third nucleic acid molecule which comprises (1) a first region complementary to at least a portion of first nonhybridizing region and (2) a second region at least a portion of second nonhybridizing region, optionally wherein the third nucleic acid molecule further comprises a spacer region between the first and second complementary regions. In some embodiments, the first and second nucleic acids and the third nucleic acid molecule are DNA molecules and the target nucleic acid is an RNA (e.g., mRNA) molecule. In some embodiments, the first and second nucleic acids are DNA molecules and the target nucleic acid is a DNA (e.g., cDNA or genomic DNA) molecule. In some embodiments, the hybridization complex further comprises the target nucleic acid hybridized to the first and second nucleic acids. In some embodiments, the first nucleic acid molecule is any as described herein. In some embodiments, the second nucleic acid molecule is any as described herein. In some embodiments, the third nucleic acid molecule is any as described herein.

In some embodiments, provided herein is a kit comprising a first nucleic acid and a second nucleic acid, wherein: the first nucleic acid comprises a first hybridizing region, and a first nonhybrizing region, the second nucleic acid comprises a second hybridizing region and a second nonhybridizing region, and the first and second nucleic acid are capable of hybridizing to a target nucleic acid, wherein the first and second hybridizing regions hybridize to the target region and the first and second nonhybridizing regions do not hybridize to the target nucleic acid. In some embodiments, the first and second nucleic acids are DNA molecules and the target nucleic acid is a DNA (e.g., cDNA or genomic DNA) molecule. In some embodiments, the first and second nucleic acids are DNA molecules and the target nucleic acid is an RNA (e.g., mRNA) molecule. In some embodiments, the kit further comprises the target nucleic acid hybridized to the first and second nucleic acids. In some embodiments, the first nucleic acid and/or the second nucleic comprises one or more barcode sequences. In some embodiments, the first nucleic acid and/or the second nucleic comprises one or more sequencing domain. In some embodiments, the first nucleic acid molecule is any as described herein. In some embodiments, the second nucleic acid molecule is any as described herein. In some embodiments, the third nucleic acid molecule is any as described herein.

In some embodiments, provided herein is a kit comprising a first nucleic acid, a second nucleic acid, and a third nucleic acid molecule, wherein: the first nucleic acid comprises a first hybridizing region, and a first nonhybrizing region, the second nucleic acid comprises a second hybridizing region and a second nonhybridizing region, and the first and second nucleic acid are capable of hybridizing to a target nucleic acid, wherein the first and second hybridizing regions hybridize to the target region and first and second nonhybridizing regions hybridize to the third nucleic acid molecule which comprises (1) a first region complementary to at least a portion of first nonhybridizing region and (2) a second region at least a portion of second nonhybridizing region, optionally wherein the third nucleic acid molecule further comprises a spacer region between the first and second complementary regions. In some embodiments, the first and second nucleic acids and the third nucleic acid molecule are DNA molecules and the target nucleic acid is an RNA (e.g., mRNA) molecule. In some embodiments, the first and second nucleic acids are DNA molecules and the target nucleic acid is a DNA (e.g., cDNA or genomic DNA) molecule. In some embodiments, the hybridization complex further comprises the target nucleic acid hybridized to the first and second nucleic acids. In some embodiments, the kit further comprises the third nucleic acid molecule. In some embodiments, the first and second polynucleotides and the third nucleic acid molecule are DNA molecules and the target nucleic acid is an RNA (e.g., mRNA) molecule. In some embodiments, the first polynucleotide, the second polynucleotide, and/or the third nucleic acid molecule comprises one or more barcode sequences. In some embodiments, the first nucleic acid, the second nucleic and/or the third nucleic acid molecule comprises one or more barcode sequences. In some embodiments, the first nucleic acid, the second nucleic and/or the third nucleic acid molecule comprises one or more sequencing domain. In some embodiments, the first nucleic acid molecule is any as described herein. In some embodiments, the second nucleic acid molecule is any as described herein. In some embodiments, the third nucleic acid molecule is any as described herein.

The various components of the kit may be present in separate containers or certain compatible components may be precombined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for embedding the biological sample. In some embodiments, the kits contain reagents, such as enzymes and buffers for ligation and/or amplification, such as ligases and/or polymerases. In some aspects, the kit can also include any of the reagents described herein, e.g., wash buffer, and ligation buffer. In some embodiments, the kits contain reagents for detection and/or sequencing, such as barcode detection probes or detectable labels. In some embodiments, the kits optionally contain other components, for example: nucleic acid primers, enzymes and reagents, buffers, nucleotides, modified nucleotides, reagents for additional assays.

Also provided herein are methods of using the compositions and/or kits disclosed herein. In some embodiments, provided herein is a method for analyzing a target nucleic acid molecule, comprising: (a) providing said target nucleic acid molecule, a first nucleic acid molecule and a second nucleic acid molecule, wherein: said first nucleic acid molecule comprises (i) a first hybridizing region having a first sequence hybridized to a first target sequence of said target nucleic acid molecule and (ii) a first nonhybridizing region at a first end of said first nucleic acid molecule that is not hybridized with said target nucleic acid molecule; and said second nucleic acid molecule comprises (i) a second hybridizing region hybridized to a second target sequence of said target nucleic acid molecule and (ii) a second nonhybridizing region at a second end of said second nucleic acid molecule that is not hybridized with said target nucleic acid molecule; and (b) coupling said first end and said second end to one another, thereby generating a nucleic acid product.

In any of the embodiments disclosed herein, the coupling can comprise coupling said first end and said second end to one another via a nucleic acid extension reaction. In any of the embodiments disclosed herein, the coupling can comprise coupling said first end and said second end to one another via a nucleic acid ligation reaction. In any of the embodiments disclosed herein, the coupling can comprise coupling said first end and said second end to one another via a hybridization reaction. In any of the embodiments disclosed herein, the coupling can comprise coupling said first end and said second end to one another via a nucleic acid extension reaction and a nucleic acid ligation reaction. In any of the embodiments disclosed herein, the coupling can comprise coupling said first end and said second end to one another via a hybridization reaction and a nucleic acid ligation reaction.

In any of the embodiments disclosed herein, prior to or during the coupling step, said first end of said first nucleic acid molecule and said second end of said second nucleic acid molecule can be adjacent. In any of the embodiments disclosed herein, prior to or during the coupling step, said first end of said first nucleic acid molecule and said second end of said second nucleic acid molecule can be separated by a gap of no more than 100 nucleotides.

In any of the embodiments disclosed herein, said first hybridizing region can be at a first opposite end of said first nucleic acid molecule from said first nonhybridizing region. In any of the embodiments disclosed herein, said second hybridizing region can be at a second opposite end of said second nucleic acid molecule from said second nonhybridizing region.

In any of the embodiments disclosed herein, the method may further comprise coupling said first opposite end and said second opposite end to one another. In any of the embodiments disclosed herein, coupling said first opposite end and said second opposite end to one another can occur after coupling said first end and said second end to one another. In any of the embodiments disclosed herein, coupling said first opposite end and said second opposite end to one another can occur prior to or during coupling said first end and said second end to one another. In any of the embodiments disclosed herein, coupling said first opposite end and said second opposite end to one another can comprise conducting a nucleic acid extension reaction. In any of the embodiments disclosed herein, coupling said first opposite end and said second opposite end to one another can comprise conducting a nucleic acid ligation reaction. In any of the embodiments disclosed herein, coupling said first opposite end and said second opposite end to one another can comprise conducting a nucleic acid hybridization reaction. In any of the embodiments disclosed herein, coupling said first opposite end and said second opposite end to one another can comprise conducting a nucleic acid extension reaction and a nucleic acid ligation reaction. In any of the embodiments disclosed herein, coupling said first opposite end and said second opposite end to one another can comprise conducting a nucleic acid hybridization reaction and a nucleic acid ligation reaction.

In any of the embodiments disclosed herein, prior to or during coupling said first opposite end and said second opposite end to one another, said opposite end of said first nucleic acid molecule and said opposite end of said second nucleic acid molecule can be adjacent. In any of the embodiments disclosed herein, prior to or during coupling said first opposite end and said second opposite end to one another, said opposite end of said first nucleic acid molecule and said opposite end of said second nucleic acid molecule can be separated by a gap of no more than 100 nucleotides.

In any of the embodiments disclosed herein, the method can further comprise using said nucleic acid product or derivative thereof in a nucleic acid extension reaction to generate one or more nucleic acid extension products. In any of the embodiments disclosed herein, the method can further comprise using said nucleic acid product or derivative thereof in a nucleic acid ligation reaction to generate one or more nucleic acid ligation products. In any of the embodiments disclosed herein, the method can further comprise using said nucleic acid product or derivative thereof in a nucleic acid amplification reaction to generate one or more nucleic acid amplification products.

In any of the embodiments disclosed herein, the nucleic acid product or derivative thereof can be a circular nucleic acid molecule. In any of the embodiments disclosed herein, the nucleic acid nucleic acid extension reaction can comprise a rolling circle amplification reaction. In any of the embodiments disclosed herein, the one or more nucleic acid extension products can comprise a concatemer.

In any of the embodiments disclosed herein, the method can further comprise detecting said one or more nucleic acid extension products or one or more derivatives thereof. In any of the embodiments disclosed herein, said detecting can comprise sequencing said one or more nucleic acid extension products or said one or more derivatives thereof. In any of the embodiments disclosed herein, said sequencing can comprise a sequencing-by-synthesis reaction. In any of the embodiments disclosed herein, said sequencing can comprise a sequencing-by-hybridization reaction. In any of the embodiments disclosed herein, said sequencing can comprise a sequencing-by-ligation reaction.

In any of the embodiments disclosed herein, prior to or during coupling said first end and said second end to one another, the method can further comprise hybridizing a sequence of a third nucleic acid molecule to at least a portion of said first nonhybridizing region and/or hybridizing an additional sequence of said third nucleic acid molecule to at least a portion of said second nonhybridizing region.

In any of the embodiments disclosed herein, prior to or during coupling said first end and said second end to one another, the method can further comprise hybridizing said sequence of said third nucleic acid molecule to said at least said portion of said first nonhybridizing region and hybridizing said additional sequence of said third nucleic acid molecule to said at least said portion of said second nonhybridizing region.

In any of the embodiments disclosed herein, coupling said first end and said second end to one another can comprise coupling said first end and said second end to one another via a nucleic acid extension reaction. In any of the embodiments disclosed herein, coupling said first end and said second end to one another can comprise coupling said first end and said second end to one another via a nucleic acid ligation reaction. In any of the embodiments disclosed herein, coupling said first end and said second end to one another can comprise coupling said first end and said second end to one another via a hybridization reaction. In any of the embodiments disclosed herein, coupling said first end and said second end to one another can comprise coupling said first end and said second end to one another via a nucleic acid extension reaction and a nucleic acid ligation reaction. In any of the embodiments disclosed herein, coupling said first end and said second end to one another can comprise coupling said first end and said second end to one another via a hybridization reaction and a nucleic acid ligation reaction.

In any of the embodiments disclosed herein, said sequence can comprise at least ten nucleotides. In any of the embodiments disclosed herein, said additional sequence can comprise at most ten nucleotides. In any of the embodiments disclosed herein, a duplex comprising said additional sequence hybridized to its complementary sequence can have a lower melting temperature than a duplex comprising said sequence hybridized to its complementary sequence.

In any of the embodiments disclosed herein, prior to or during coupling said first end and said second end to one another, the method can further comprise hybridizing said sequence to said first nonhybridizing region and using said sequence to conduct a nucleic acid extension reaction to generate a nucleic acid extension product. In any of the embodiments disclosed herein, said nucleic acid extension reaction can comprise a rolling circle amplification reaction. In any of the embodiments disclosed herein, said one or more nucleic acid extension products can comprise a concatemer.

In any of the embodiments disclosed herein, the method can further comprise detecting said one or more nucleic acid extension products or one or more derivatives thereof. In any of the embodiments disclosed herein, the detecting can comprise sequencing said one or more nucleic acid extension products or said one or more derivatives thereof. In any of the embodiments disclosed herein, the sequencing can comprise a sequencing-by-synthesis reaction. In any of the embodiments disclosed herein, said sequencing can comprise a sequencing-by-hybridization reaction. In any of the embodiments disclosed herein, said sequencing can comprise a sequencing-by-ligation reaction.

In any of the embodiments disclosed herein, said target nucleic acid molecule can comprise complementary deoxyribonucleic acid (cDNA) derived from reverse transcribed ribonucleic acid (RNA). In any of the embodiments disclosed herein, said target nucleic acid molecule can comprise a messenger ribonucleic acid (mRNA) molecule. In any of the embodiments disclosed herein, said target nucleic acid molecule can comprise a genomic nucleic acid molecule. In any of the embodiments disclosed herein, said target nucleic acid molecule can be immobilized to a three-dimensional (3D) matrix.

In any of the embodiments disclosed herein, said first nonhybridizing region may not have a sequence complementarity to said first target sequence. In any of the embodiments disclosed herein, said second nonhybridizing region may not have a sequence complementarity to said second target sequence. In any of the embodiments disclosed herein, said first nucleic acid molecule may comprise a sequencing primer binding site. In any of the embodiments disclosed herein, said second nucleic acid molecule may comprise a barcode domain.

XIII. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" or "fewer than" or "fewer or equal to" or the like precedes the first numerical value in a series of two or more numerical values, the term "no more than," "less than," or "less than or equal to" or "fewer than" or "fewer or equal to" applies to each of the numerical values in that series of numerical values. For example, less than or equal to 3, 2, or 1 is equivalent to less than or equal to 3, less than or equal to 2, or less than or equal to 1.

The terms "nucleic acid" or "target nucleic acid," as used herein, generally refer to a polymeric form of nucleotides of any length. A nucleic acid may comprise either deoxyribonucleotides (dNTPs) or ribonucleotides (rNTPs), or analogs thereof. A nucleic acid may be an oligonucleotide or a polynucleotide. Nucleic acids may have any three-dimensional structure and may perform any function. Non-limiting examples of nucleic acids include deoxyribonucleic acid (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation, with a functional moiety for immobilization.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, e.g., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Multiplexing" or "multiplex assay" herein may refer to an assay or other analytical method in which the presence and/or amount of multiple targets, e.g., multiple nucleic acid target sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLES

The following examples are illustrative of certain systems and methods described herein and are not intended to be limiting.

Example 1—Assembling a Multicomponent Probe for Sample Analysis

Figure 7:
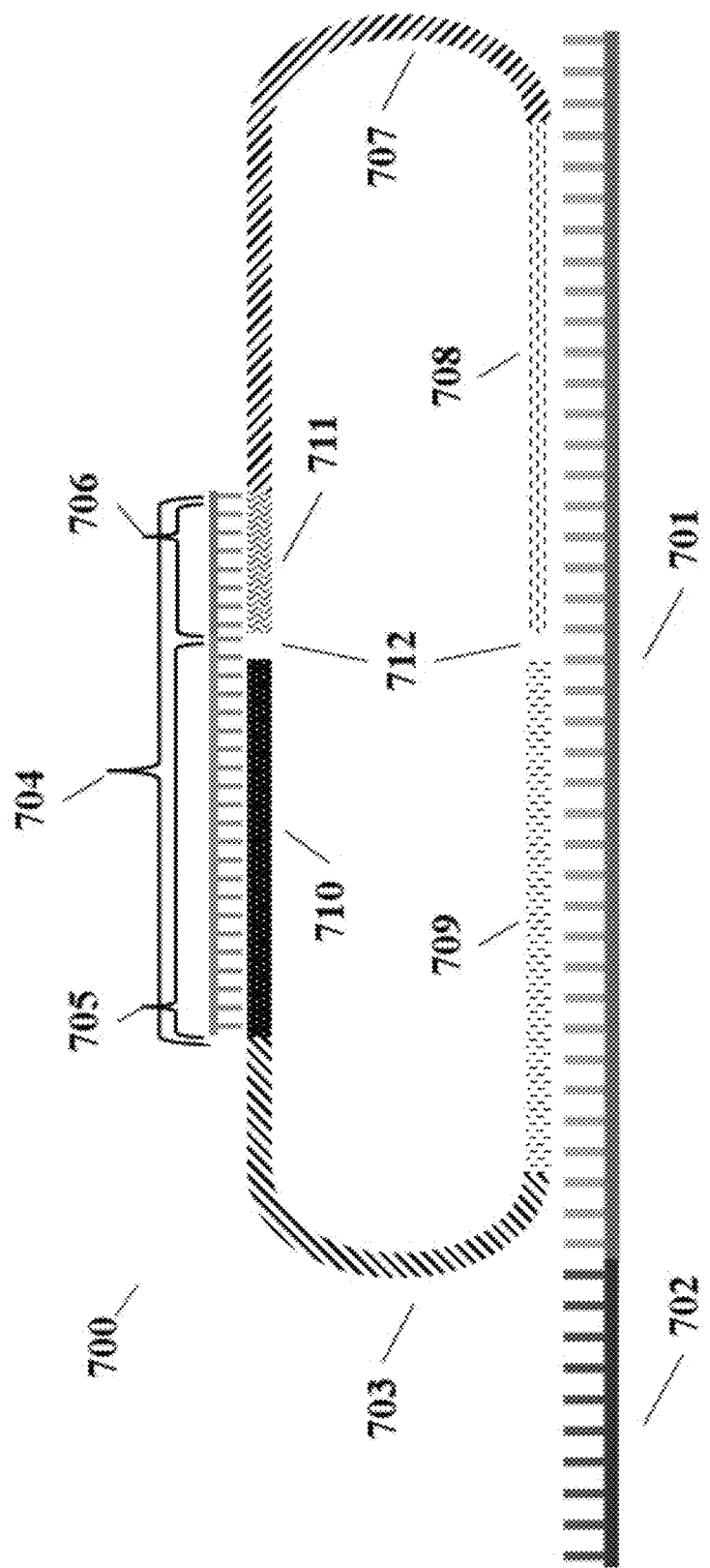
FIG. 7 is a schematic of an exemplary multicomponent probe. In some embodiments, the exemplary multicomponent probe comprises a first nucleic acid component (e.g., a first probe) comprising a first hybridizing region (e.g., a first target-hybridizing region) and a first nonhybridizing region (e.g., a first splint-hybridizing region). In some embodiments, the exemplary multicomponent probe comprises a second nucleic acid component (e.g., a second probe) comprising a second hybridizing region (e.g., a second target-hybridizing region) and a second nonhybridizing region (e.g., a second splint-hybridizing region). In some embodiments, a third nucleic acid molecule (e.g., a splint) with a sequence (e.g., a first splint sequence) complementary to the first nonhybridizing region and an additional sequence (e.g., a second splint sequence) complementary to the second nonhybridizing region.

FIG. 7 is a schematic of an exemplary multicomponent probe 700. In this example, a target nucleic acid molecule 701 can be an extended complementary DNA (cDNA) strand generated from a reverse transcription of an RNA strand, but the target molecule can be any target nucleic acid molecule (e.g., an RNA molecule). The target nucleic acid molecule 701 can be attached to reverse transcriptase (RT) primer 702. In some embodiments, the reverse transcriptase primer can function as a tethering oligo (e.g., the reverse transcriptase primer can be directly conjugated to a tethering group) or comprise a tethering domain target that hybridizes to a tethering oligo comprising a tethering group. In some embodiments, the reverse transcriptase primer can comprise a gene specific sequence that hybridizes to an mRNA of interest, and/or an oligo(dT) sequence that hybridizes to a poly-A tail sequence of an mRNA of interest. The RT primer may have been used in the generation of the cDNA strand (e.g., the cDNA strand was grown using a reverse transcriptase initiated from the RT primer). The RT primer can be secured to a 3D matrix (e.g., a 3D matrix as described elsewhere herein) via a tethering moiety (not shown). If the target nucleic acid molecule were not generated by a reverse transcriptase reaction, the target nucleic acid molecule 701 can be directly tethered to the 3D matrix.

In this example, the multicomponent probe 700 has two components (e.g., target binding regions). The first component comprises first hybridizing region 709 and first non-hybridizing region 710, which comprises first functional region 703 and does not hybridize with target nucleic acid molecule 701. Similarly, the second component comprises second hybridizing region 708 and second nonhybridizing region 711, which comprises second functional region 707 and does not hybridize with target nucleic acid molecule 701. The first and second hybridizing regions 709 and 708 can be at least partially complementary to target nucleic acid molecule 701. As shown, the first and second hybridizing regions can hybridize to the target nucleic acid molecule such that a gap 712 is present between the first and second hybridizing region and between the first and second nonhybridizing regions. The presence of the gap can be to permit sequence variations in the target nucleic acid molecule to be translated into the probe 700. For example, a first and second probe can be hybridized to the target nucleic acid molecule with a gap between them, and the gap can be in a region with a suspected sequence variation in the target nucleic acid molecule. In this example, a nucleic acid extension reaction can be performed to fill the gap, such that the sequence variation is represented in the probe for later detection. The gaps 712 can be filled and components ligated to link the first and second components into the single probe 700.

First and second functional regions 703 and 707 may comprise one or more functional domains. The one or more functional domains may be molecular barcodes (e.g., molecular barcodes for sequencing by synthesis, molecular barcodes for sequencing by ligation, molecular barcodes for sequencing by hybridization, etc.), spatial or other unique molecular identifiers (such as those of PCT publication number WO2020/076976, the disclosure of which is incorporated by reference herein in its entirety), amplification relevant domains (e.g., for formation of an in situ clonally amplified sequence template (e.g., polymerase colony ("polony") or rolling circle amplification amplicon), for three-dimensional indexing readout (e.g., T7RNAP/T7RNA terminator sequences for expression of RNA off of the rolling circle amplification amplicon), domains for linking the probe and/or the amplicon to the three-dimensional matrix (e.g., for direct RNA capture where the RNA lacks a cDNA primed by a reverse transcriptase primer containing a functional tethering moiety which may be associated with the probe complex by a second functional group (e.g., oligonucleotide) binding to the first or second functional regions), domains for compaction of the amplicon during amplification (e.g., compaction oligonucleotides as described by Claussen et al. Compaction of rolling circle amplification products increases signal integrity and signal-to-noise ratio, Scientific Reports, DOI number 10.1038/srep12317, the disclosure of which is incorporated by reference in its entirety), domains for forming intra-amplicon linkages (e.g., chemical or nucleic acid bridges or crosslinks between one or more domains or moieties present within the amplicon), spacer domains (e.g., domains which provide a determined final length of the assembled probe complex, which final length may be optimized for the amplification as shown by Joffroy et al. Rolling circle amplification shows a sinusoidal template length-dependent amplification bias, Nucleic Acids Research, DOI number 10.1093/nar/gkx1238, the disclosure of which is incorporated by reference in its entirety), or the like, or any combination thereof.

A splint molecule 704 can comprise a first complementary region 705 and a second complementary region 706. The first complementary region 705 can be complementary to the first nonhybridizing region 710, while the second complementary region 706 can be complementary to the second nonhybridizing region 711. As shown, the first complementary region 705 can be longer than the second complementary region 706. Alternatively, the first and second complementary regions can be the same length, or the second complementary region can be longer than the first complementary region. The different lengths of regions 705 and 706 can impart different binding kinetics and/or duplex stability to them. In this example, region 705 is stably hybridized to the first nonhybridizing region 710 (e.g., forming a first duplex). However, the shorter length of region 706 can result in a more dynamic binding to the second nonhybridizing region 711 (e.g., forming a second duplex). As such, the splint molecule 704 can stably bind to the first probe component in solution while not stably binding to the second probe component. This can prevent circularization of the first and second components without the presence of the target molecule and/or formation of pre-circularized complexes in absence of the target molecule, as the dynamic binding of regions 706 and 711 can decrease the likelihood that the two components are adjacent for ligation without the presence of the target nucleic acid molecule. Once the first and second probe components are hybridized to the target nucleic acid molecule, even a small binding equilibrium between the second nonhybridizing region 711 and the second complementary region 706 can result in sufficient bound time for the gap 712 between them to be ligated. In some embodiments, each of the plurality of probe components are introduced in a sequential order, and the splint component can stably hybridize to both components. For example, the first probe component can be introduced to the target nucleic acid molecule, the excess first probe component washed away, and the splint molecule and the second probe component can then be introduced. Because the plurality of probe components can be introduced sequentially, and excess probe components can be washed away prior to the introduction of the other probe components, the likelihood of solution formation of the probe can be lowered.

The first nonhybridizing region 710 can also be an amplification primer binding site. The amplification primer can be configured to bind a polymerase to the probe 700. Due to exonuclease properties of some polymerases, the terminal end of region 705 can comprise exonuclease resistant properties as described elsewhere herein. The polymerase can perform a rolling circle amplification of the probe to generate a concatemer comprising a plurality of linearized repeats of a complement of probe 700. The polymerase can comprise strand displacement activity to remove the probe 700 from the target nucleic acid molecule 701. For example, once the components of probe 700 have been ligated to form a circular probe, a strand displacement polymerase can bind to the first nonhybridizing region 710 and begin an amplification reaction around the probe, displacing the probe from the target molecule as the polymerase goes around the probe.

The second nonhybridizing region 711 can also be a barcode domain. The barcode domain can be a predetermined sequence configured to bind to a barcode oligonucleotide. The barcode oligonucleotide can be coupled to a detectable label (e.g., a dye), thus permitting identification of the barcode sequence. Since the barcode sequence is predetermined to be related to a particular target nucleic acid molecule, identifying the barcode sequence results in the identification of the target nucleic acid molecule. In some embodiments, the barcode domain is sequenced to identify the barcode domain. For example, the barcode domain can be sequenced by synthesis, thus identifying both the barcode domain and the related hybridizing regions.

Decomposing the probe into a plurality of probe components can provide a variety of benefits over using a single probe. One such benefit can be a reduced false positive rate. Since the barcode region and the primer region can be separated, or substantially separated (e.g., fragmented between the different probe components such that the fragmented regions are not sufficient for the operation of the regions, but are sufficient when the regions are combined), onto different probe components, each component, if self-circularized, can be not competent for detection. For example, a self-circularized probe component without a primer region does not undergo amplification, while a self-circularized probe component without a barcode region but having a primer region does not have the components sufficient for detection. Even if one probe component is sufficient for detection (e.g., comprises both a primer and a barcode region), the use of a plurality of probe components can reduce the false positive rate by reducing the rate of self-circularization. The self-circularization rate can be related to the length of the nucleic acid undergoing self-circularization. For example, the ends of a nucleic acid molecule of sufficient length can be viewed as two separate nucleic acid molecules with a high effective concentration due to their physical proximity. In this example, the long length of the nucleic acid molecule can sufficiently reduce the bending strain of the nucleic acid molecule to permit self-circularization. Alternatively, two shorter probe components can have a higher bending strain due to their shorter length, which can reduce the occurrence of self-circularization.

Another benefit can be a reduction in the number of probes used for multiplexed detection. For example, multiple target nucleic acid molecules with similar sequences (e.g., nucleic acids with insertions, deletions, single nucleotide polymorphisms/variations, alternative splicings, etc.) can be detected with a reduced number of probes, as portions of the probes can be reused between the different targets. For example, a first component complementary to a conserved domain among the similar sequences can be coupled to a plurality of different second components each corresponding to the different variants to be detected. In this example, the plurality of second components can comprise the barcode region such that each of the plurality of second components can be related to the corresponding variant, while the first component can have a primer region.

Another benefit can be a faster reaction time. The diffusion rate of a probe can depend on a variety of properties of the probe, such as the length, strandedness (e.g., single stranded, double stranded), molecular weight, or the like. For example, a longer probe can diffuse slower through a solution or 3D matrix, leading to long cycle times to permit equilibration, but shorter probe components can diffuse faster to enable shorter cycle times. Hybridization reaction kinetics can be limited by diffusion, so improving diffusion speed can result in faster hybridization. Similarly, the rate of removal of a probe during a washing operation can be limited by diffusion, so shorter probe components can permit shorter washing operations and increased time efficiency.

Another benefit can be an improvement of the quality of the probe components as compared to full length probes. Because the chemical techniques used to generate probes and probe components can have inherent sequence error rates for each base of the nucleic acid molecule, shorter probes can have lower numbers of errors than longer probes. By combining a plurality of shorter probe components into a longer probe, the rate of errors in the longer probe can be lowered as compared to a longer probe that was not assembled from probe components.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method for analyzing a sample, comprising:
   (a) forming a hybridization complex comprising a first probe, a second probe, a splint, and a target nucleic acid molecule in the sample, wherein:
      the target nucleic acid molecule comprises a first target sequence and a second target sequence,
      the splint comprises a first splint sequence and second splint sequence,
      the first probe comprises, from one end to another: (i) a first splint-hybridizing region forming a first duplex with the first splint sequence and (ii) a first target-hybridizing region hybridized to the first target sequence,
      the second probe comprises, from one end to another: (i) a second target-hybridizing region hybridized to the second target sequence, (ii) a barcode region corresponding to the target nucleic acid molecule or a sequence thereof, and (iii) a second splint-hybridizing region forming a second duplex with the second splint sequence, and
      the first duplex and the second duplex differ in stability;
   (b) generating a circular probe by (i) ligating the first target-hybridizing region and the second target-hybridizing region and (ii) ligating the first splint-hybridizing region and the second splint-hybridizing region; and
   (c) determining a sequence of the barcode region or complement thereof in the circular probe or an amplification product thereof,
   thereby detecting the target nucleic acid molecule in the sample.

2. The method of claim 1, wherein the target nucleic acid molecule is a cDNA tethered to a three-dimensional (3D) matrix embedding the sample, and/or the first and second probes do not comprise ribonucleotides.

3. The method of claim 1, wherein forming the hybridization complex comprises:
   (i) contacting the sample with the first probe and the second probe to allow probe hybridization to the target nucleic acid molecule;
   (ii) washing the sample; and
   (iii) contacting the sample with the splint to allow splint hybridization to the first and second probes.

4. The method of claim 1, wherein the first duplex is less stable than the second duplex.

5. The method of claim 1, wherein the first duplex is more stable than the second duplex.

6. The method of claim 5, wherein the melting temperature of the first duplex is at least 1° C., at least 2° C., at least 5° C., at least 10° C., or at least 15° C. higher than the melting temperature of the second duplex.

7. The method of claim 5, wherein the first duplex is at least 1, at least 2, at least 5, at least 10, or at least 15 base pairs longer than the second duplex.

8. The method of claim 1, wherein the first splint-hybridizing region is at least 10 nucleotides and the second splint-hybridizing region is shorter than 10 nucleotides in length.

9. The method of claim 1, wherein the barcode region and the second splint-hybridizing region do not overlap.

10. The method of claim 9, wherein the barcode region and the second splint-hybridizing region are connected by a phosphodiester bond.

11. The method of claim 1, wherein the barcode region and the second splint-hybridizing region partially or wholly overlap with each other.

12. The method of claim 1, wherein the first probe does not comprise a barcode region or a portion thereof.

13. The method of claim 1, wherein the first splint-hybridizing region does not comprise a barcode region or a portion thereof.

14. The method of claim 1, wherein the first splint-hybridizing region comprises a common primer binding site among a plurality of first probes each hybridizing to a different first target sequence.

15. The method of claim 1, wherein determining the sequence of the barcode region comprises performing sequencing by ligation using the splint or a portion thereof as primer.

16. The method of claim 1, further comprising performing rolling circle amplification (RCA) using the splint or a portion thereof as primer and the circular probe as template to generate an RCA product of the circular probe.

17. The method of claim 16, wherein determining the sequence of a complement of the barcode region in the RCA product comprises performing sequencing by ligation, sequencing by hybridization, and/or sequencing by synthesis.

18. A method for analyzing a sample, comprising:
(a) reverse transcribing an RNA molecule in the sample to produce a cDNA molecule comprising a tethering moiety;
(b) embedding the sample containing the cDNA molecule in a three-dimensional (3D) matrix, wherein the tethering moiety is configured to tether the cDNA molecule to the 3D matrix;
(c) contacting the sample embedded in the 3D matrix with a first probe and a second probe, wherein:
the first probe comprises, in the 5' to 3' direction: (i) a first splint-hybridizing region, (ii) a linker region, and (iii) a first target-hybridizing region that hybridizes to a first target sequence in the cDNA molecule, and
the second probe comprises, in the 5' to 3' direction: (i) a second target-hybridizing region that hybridizes to a second target sequence in the cDNA molecule, (ii) a barcode region corresponding to the RNA molecule, and (iii) a second splint-hybridizing region;
(d) contacting the sample embedded in the 3D matrix with a splint comprising a first splint sequence and second splint sequence, wherein the first splint sequence and the first splint-hybridizing region form a first duplex and the second splint sequence and the second splint-hybridizing region form a second duplex, and wherein the first duplex is more stable than the second duplex;
(e) generating a circular probe hybridized to the cDNA molecule and the splint by (i) ligating the first target-hybridizing region and the second target-hybridizing region and (ii) ligating the first splint-hybridizing region and the second splint-hybridizing region;
(f) generating a rolling circle amplification (RCA) product of the circular probe in the sample, wherein the RCA product comprises one or more modified nucleotides configured to tether the RCA product to the 3D matrix; and
(g) sequencing a complement of the barcode region in the RCA product tethered to the 3D matrix,
thereby detecting the RNA molecule in the sample.

19. The method of claim 18, wherein the sample is a tissue sample, and wherein the method further comprises, between (b) and (c):
i) clearing the sample embedded in the 3D matrix; and
ii) degrading the RNA molecule.

20. The method of claim 18, wherein the RCA product comprises multiple copies of a unit sequence comprising a complement of the linker region, and the method further comprises contacting the RCA product with one or more oligonucleotide probes that hybridize to complements of the linker region in different copies of the unit sequence.

* * * * *